(12) United States Patent
Stamatopoulos et al.

(10) Patent No.: US 9,814,438 B2
(45) Date of Patent: Nov. 14, 2017

(54) METHODS AND APPARATUS FOR PERFORMING DYNAMIC RESPIRATORY CLASSIFICATION AND TRACKING

(71) Applicant: BreathResearch, Inc., Walnut Creek, CA (US)

(72) Inventors: Charalampos Christos Stamatopoulos, Athens (GR); Panagiotis Giotis, Berlin (DE); Nirinjan Bikko Yee, Walnut Creek, CA (US)

(73) Assignee: BREATH RESEARCH, INC., Walnut Creek, CA (US)

( * ) Notice: Subject to any disclaimer, the term of this patent is extended or adjusted under 35 U.S.C. 154(b) by 879 days.

(21) Appl. No.: 13/920,655

(22) Filed: Jun. 18, 2013

(65) Prior Publication Data

US 2014/0155773 A1 Jun. 5, 2014

Related U.S. Application Data

(60) Provisional application No. 61/661,267, filed on Jun. 18, 2012.

(51) Int. Cl.
*A61B 7/00* (2006.01)
*A61B 7/04* (2006.01)
*A61B 5/08* (2006.01)
*A61B 5/00* (2006.01)

(52) U.S. Cl.
CPC ............... *A61B 7/003* (2013.01); *A61B 7/04* (2013.01); *A61B 5/0816* (2013.01); *A61B 5/0823* (2013.01); *A61B 5/0826* (2013.01); *A61B 5/6819* (2013.01); *A61B 5/6831* (2013.01); *A61B 5/725* (2013.01); *A61B 5/7278* (2013.01); *A61B 5/742* (2013.01); *A61B 5/7465* (2013.01)

(58) Field of Classification Search
None
See application file for complete search history.

(56) References Cited

U.S. PATENT DOCUMENTS

| | | |
|---|---|---|
| 3,991,304 A | 11/1976 | Hillsman |
| 4,063,550 A | 12/1977 | Tiep |
| 4,064,869 A | 12/1977 | Defares et al. |

(Continued)

FOREIGN PATENT DOCUMENTS

| | | |
|---|---|---|
| EP | 0145160 | 6/1985 |
| EP | 0804938 | 11/1997 |

(Continued)

OTHER PUBLICATIONS

Extended European Search Report dated Aug. 8, 2011 in EP Application No. 06849045, 7 Pages.

*Primary Examiner* — Jacqueline Cheng
*Assistant Examiner* — Jairo Portillo

(57) ABSTRACT

A method for performing dynamic classification of a breathing session is disclosed. The method comprises capturing breathing sounds of a subject using a microphone. Further, it comprises recognizing a plurality of breath cycles and a plurality of breath phases within each of the plurality of breath cycles from the breathing sounds. It also comprises detecting characteristics regarding the plurality of breath cycles and the plurality of breath phases. Finally, it comprises extracting metrics concerning a breath pattern quality of the subject using the detected characteristics.

17 Claims, 21 Drawing Sheets

(56) References Cited

U.S. PATENT DOCUMENTS

| | | | |
|---|---|---|---|
| 4,143,648 A | 3/1979 | Cohen et al. | |
| 4,215,431 A | 7/1980 | Nady | |
| 4,220,142 A | 9/1980 | Rosen et al. | |
| 4,337,445 A | 6/1982 | Akagiri | |
| 4,644,330 A | 2/1987 | Dowling | |
| 4,798,538 A | 1/1989 | Yagi | |
| 4,848,360 A | 7/1989 | Palsgard et al. | |
| 4,924,876 A | 5/1990 | Cameron | |
| 4,981,295 A | 1/1991 | Belman et al. | |
| 5,076,281 A | 12/1991 | Gavish | |
| 5,137,601 A | 8/1992 | Hsu | |
| 5,444,786 A | 8/1995 | Raviv | |
| 5,477,667 A | 12/1995 | Bryant | |
| 5,477,867 A | 12/1995 | Balkanyi | |
| 5,633,473 A | 5/1997 | Mori et al. | |
| 5,779,484 A | 7/1998 | Lampotang et al. | |
| 5,800,337 A | 9/1998 | Gavish | |
| 5,810,722 A | 9/1998 | Heikkila | |
| 5,879,313 A | 3/1999 | Raviv et al. | |
| 5,899,203 A | 5/1999 | Defares et al. | |
| 5,936,464 A | 8/1999 | Grondahl | |
| 6,027,463 A | 2/2000 | Moriyasu | |
| 6,056,703 A * | 5/2000 | Sandler | A61B 7/008 600/593 |
| 6,064,964 A | 5/2000 | Yamamoto et al. | |
| 6,090,037 A | 7/2000 | Gavish | |
| 6,134,331 A | 10/2000 | B.ae butted.kgaard | |
| 6,142,950 A | 11/2000 | Allen et al. | |
| 6,261,238 B1 * | 7/2001 | Gavriely | A61B 5/087 600/532 |
| 6,273,728 B1 | 8/2001 | van Meurs et al. | |
| 6,411,850 B1 * | 6/2002 | Kay | A61N 1/36521 607/19 |
| 6,423,013 B1 | 7/2002 | Bakker et al. | |
| 6,626,843 B2 | 9/2003 | Hillsman | |
| 6,662,032 B1 | 12/2003 | Gavish et al. | |
| 6,889,033 B2 | 5/2005 | Bongfeldt | |
| 6,935,335 B1 | 8/2005 | Lehrman et al. | |
| 7,006,650 B1 | 2/2006 | Wild | |
| 7,390,304 B2 | 6/2008 | Chen et al. | |
| 7,554,028 B2 | 6/2009 | Fujii | |
| 7,559,903 B2 | 7/2009 | Moussavi et al. | |
| 7,785,249 B2 | 8/2010 | Schachter et al. | |
| 8,092,381 B2 | 1/2012 | Edwards | |
| 8,768,489 B2 | 7/2014 | Thieberger et al. | |
| 8,834,364 B2 | 9/2014 | Heneghan et al. | |
| 2002/0090921 A1 | 7/2002 | Midtgaard et al. | |
| 2003/0072457 A1 | 4/2003 | Grasfield et al. | |
| 2003/0130595 A1 | 7/2003 | Mault | |
| 2003/0212338 A1 | 11/2003 | Linck et al. | |
| 2004/0186390 A1 | 9/2004 | Ross et al. | |
| 2004/0225226 A1 * | 11/2004 | Lehrman | A61B 7/003 600/529 |
| 2004/0260191 A1 | 12/2004 | Stubbs et al. | |
| 2005/0032496 A1 | 2/2005 | Saeki | |
| 2005/0068211 A1 | 3/2005 | Arai et al. | |
| 2005/0124906 A1 | 6/2005 | Childre et al. | |
| 2005/0192508 A1 | 9/2005 | Lange et al. | |
| 2006/0009971 A1 * | 1/2006 | Kushner | G10L 17/26 704/231 |
| 2006/0063981 A1 * | 3/2006 | Sotos | A61B 5/04 600/301 |
| 2006/0107824 A1 | 5/2006 | Bando et al. | |
| 2006/0198533 A1 | 9/2006 | Wang et al. | |
| 2007/0117075 A1 | 5/2007 | Gordon et al. | |
| 2007/0167855 A1 | 7/2007 | Shin et al. | |
| 2007/0173730 A1 | 7/2007 | Bikko | |
| 2007/0239225 A1 | 10/2007 | Saringer | |
| 2007/0282174 A1 | 12/2007 | Sabatino | |
| 2007/0282212 A1 * | 12/2007 | Sierra | A61B 5/0205 600/529 |
| 2008/0071137 A1 | 3/2008 | Schachter et al. | |
| 2008/0082017 A1 * | 4/2008 | Savic | A61B 7/003 600/529 |
| 2008/0109965 A1 | 5/2008 | Mossbeck | |
| 2009/0118631 A1 | 5/2009 | Gavish et al. | |
| 2009/0312660 A1 * | 12/2009 | Guarino | A61B 5/08 600/529 |
| 2010/0069774 A1 | 3/2010 | Bingham et al. | |
| 2010/0174200 A1 | 7/2010 | Wood et al. | |
| 2010/0240945 A1 * | 9/2010 | Bikko | G10L 21/00 600/28 |
| 2010/0262031 A1 | 10/2010 | Fu et al. | |
| 2011/0125045 A1 * | 5/2011 | Scholz | A61B 5/087 600/538 |
| 2011/0230778 A1 * | 9/2011 | Lai | A61B 5/0816 600/529 |
| 2011/0295138 A1 * | 12/2011 | Lai | A61B 7/003 600/529 |
| 2011/0295139 A1 * | 12/2011 | Yang | A61B 5/0816 600/529 |
| 2012/0065978 A1 * | 3/2012 | Villavicencio | G10L 13/033 704/258 |
| 2012/0071777 A1 * | 3/2012 | MacAuslan | A61B 5/0823 600/529 |
| 2014/0350361 A1 | 11/2014 | De Chazal et al. | |

FOREIGN PATENT DOCUMENTS

| | | |
|---|---|---|
| EP | 2925217 | 10/2015 |
| JP | 5241993 | 7/2013 |
| WO | 9814116 | 4/1998 |
| WO | 2001023040 | 4/2001 |
| WO | 2005089856 | 9/2005 |
| WO | 2011132118 | 10/2011 |
| WO | 2014083079 | 6/2014 |
| WO | WO2014083079 | 6/2014 |

* cited by examiner

Respiratory Rate, Breath Intensity, Inhalation Intensity, plotted along with heart rate and effort in watts.

METHODS AND APPARATUS FOR PERFORMING DYNAMIC RESPIRATORY CLASSIFICATION AND TRACKING

CROSS-REFERENCE TO RELATED APPLICATIONS

This application claims priority from U.S. Provisional Application No. 61/661,267, filed Jun. 18, 2012, entitled "Methods and Apparatus To Determine Ventilatory and Respiratory Compensation Thresholds," assigned to the assignee of the present application and the entire disclosure of which is incorporated herein by reference.

FIELD OF THE INVENTION

Embodiments according to the present invention relate to dynamically analyzing breathing sounds using an electronic device.

BACKGROUND OF THE INVENTION

In conventional respiratory analysis systems, in order determine an athlete's Ventilatory Threshold ("VT") and Respiratory Compensation Threshold ("RCT"), a complex medical device (often referred to as gas or metabolic analyzers) and the personnel to conduct the test are required. This is often cost prohibitive. One additional scientific way to measure VT and RCT is to use a blood lactate analysis. However, this is an invasive medical procedure. Another method to measure VT and RCT is to use the Foster talk test, but, in this case, the athlete has too much room for personal and subjective interpretation and thus the results may not be as reliable as the more scientific methods.

Further, while respiratory analysis has conventionally been used to perform diagnosis for certain disorders, e.g., airway constrictions and pathologies etc., conventional methods of performing respiratory analysis are typically cumbersome to use because they employ intricate apparatuses for capturing and analyzing breathing activity. In addition, conventional methods of performing respiratory analysis do not take into account full breath cycles; they do not analyze the different breath phases in a breathing cycle, namely, inhale, transition, exhale and rest.

BRIEF SUMMARY OF THE INVENTION

Accordingly, there is a need for improved methods and apparatus to determine VT and RCT. Using the beneficial aspects of the systems described, without their respective limitations, embodiments of the present invention provide novel solutions to the challenges inherent in determining VT and RCT in a non-invasive and accurate fashion.

Further, there is a need for a method and apparatus for performing respiratory analysis that uses inexpensive and readily available means for capturing and reporting breathing activity. Further, there is a need for a method and apparatus that takes into account full breath cycles when performing respiratory analysis. In other words, there is a need for a method and apparatus for performing respiratory analysis that is operable to analyze the different breath phases in a breathing cycle, namely, inhale, transition, exhale and rest.

In one embodiment, a method for performing acoustic dynamic classification of a breathing session is disclosed. The method comprises capturing breathing sounds of a subject using a microphone. Further, it comprises recognizing a plurality of breath cycles and a plurality of breath phases within each of the plurality of breath cycles from the breathing sounds. It also comprises detecting characteristics regarding the plurality of breath cycles and the plurality of breath phases. Finally, it comprises extracting metrics concerning a breath pattern quality of the subject using the detected characteristics.

In a different embodiment, a computer-readable storage medium having stored thereon, computer executable instructions that, if executed by a computer system cause the computer system to perform a method for performing acoustic dynamic classification of a breathing session. The method comprises capturing breathing sounds of a subject using a microphone. Further, it comprises recognizing a plurality of breath cycles and a plurality of breath phases within each of the plurality of breath cycles from the breathing sounds. It also comprises detecting characteristics regarding the plurality of breath cycles and the plurality of breath phases. Finally, it comprises extracting metrics concerning a breath pattern quality of the subject using the detected characteristics.

In another embodiment, an apparatus for performing acoustic dynamic classification of a breathing session is disclosed. The apparatus comprises a microphone for capturing breathing sounds of a subject. It also comprises a memory comprises an application for performing dynamic classification of a breathing session stored therein. Further, it comprises a processor coupled to the memory and the microphone, the processor being configured to operate in accordance with the application to: (a) process the breathing sounds to generate an audio respiratory signal; (b) recognize a plurality of breath cycles and a plurality of breath phases within each of the plurality of breath cycles from the audio respiratory signal; (c) detect characteristics regarding the plurality of breath cycles and the plurality of breath phases; and (d) extract metrics concerning a breath pattern quality of the subject using the characteristics.

The following detailed description together with the accompanying drawings will provide a better understanding of the nature and advantages of the present invention.

BRIEF DESCRIPTION OF THE DRAWINGS

Embodiments of the present invention are illustrated by way of example, and not by way of limitation, in the figures of the accompanying drawings and in which like reference numerals refer to similar elements.

Figure 1:
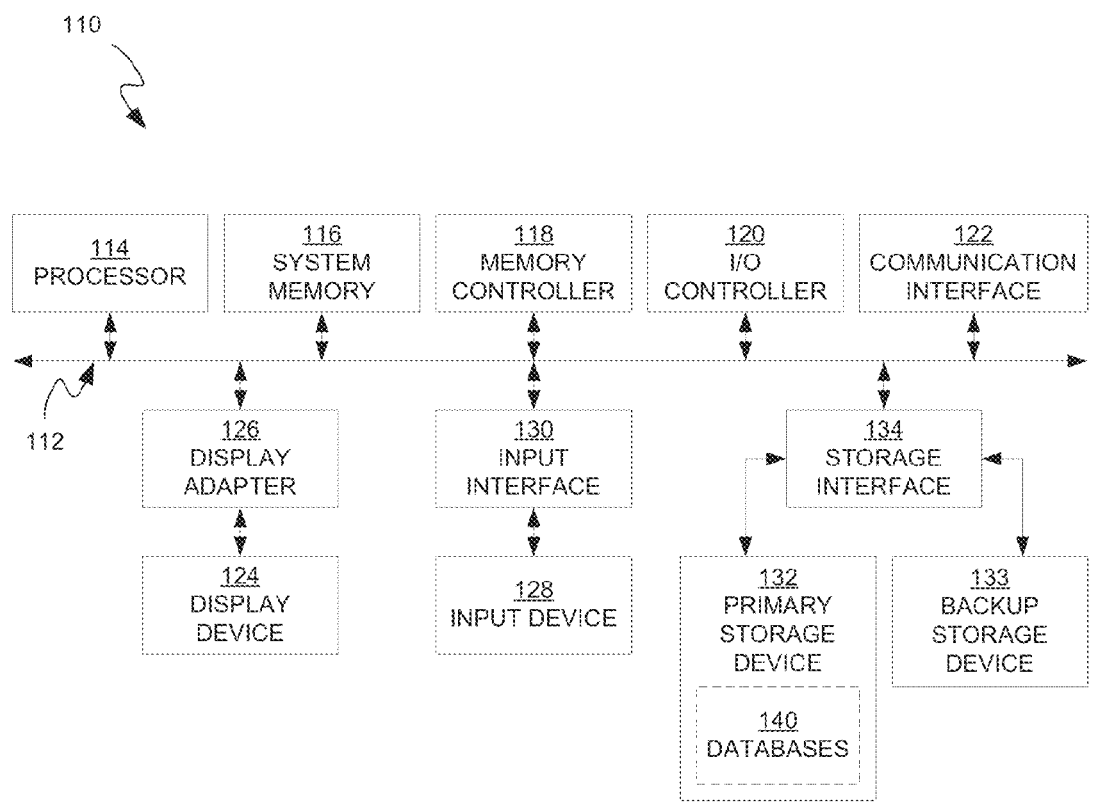
FIG. 1 is an exemplary computer system in accordance with embodiments of the present invention.

In the figures, elements having the same designation have the same or similar function.

DETAILED DESCRIPTION OF THE INVENTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "analyzing," "generating," "classifying," "filtering," "calculating," "performing," "extracting," "recognizing," "capturing," or the like, refer to actions and processes (e.g., flowchart 900 of FIG. 9) of a computer system or similar electronic computing device or processor (e.g., system 110 of FIG. 1). The computer system or similar electronic computing device manipulates and transforms data represented as physical (electronic) quantities within the computer system memories, registers or other such information storage, transmission or display devices.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer-readable storage media and communication media; non-transitory computer-readable media include all computer-readable media except for a transitory, propagating signal. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared, and other wireless media. Combinations of any of the above can also be included within the scope of computer-readable media.

FIG. 1 is a block diagram of an example of a computing system 110 used to perform respiratory acoustic analysis and capable of implementing embodiments of the present disclosure. Computing system 110 broadly represents any single or multi-processor computing device or system capable of executing computer-readable instructions. Examples of computing system 110 include, without limitation, workstations, laptops, client-side terminals, servers, distributed computing systems, handheld devices, or any other computing system or device. In its most basic configuration, computing system 110 may include at least one processor 114 and a system memory 116.

Processor 114 generally represents any type or form of processing unit capable of processing data or interpreting and executing instructions. In certain embodiments, processor 114 may receive instructions from a software application or module. These instructions may cause processor 114 to perform the functions of one or more of the example embodiments described and/or illustrated herein.

System memory 116 generally represents any type or form of volatile or non-volatile storage device or medium capable of storing data and/or other computer-readable instructions. Examples of system memory 116 include, without limitation, RAM, ROM, flash memory, or any other suitable memory device. Although not required, in certain embodiments computing system 110 may include both a volatile memory unit (such as, for example, system memory 116) and a non-volatile storage device (such as, for example, primary storage device 132).

Computing system 110 may also include one or more components or elements in addition to processor 114 and system memory 116. For example, in the embodiment of FIG. 1, computing system 110 includes a memory controller 118, an input/output (I/O) controller 120, and a communication interface 122, each of which may be interconnected via a communication infrastructure 112. Communication infrastructure 112 generally represents any type or form of infrastructure capable of facilitating communication between one or more components of a computing device. Examples of communication infrastructure 112 include, without limitation, a communication bus (such as an Industry Standard Architecture (ISA), Peripheral Component Interconnect (PCI), PCI Express (PCIe), or similar bus) and a network.

Memory controller 118 generally represents any type or form of device capable of handling memory or data or controlling communication between one or more components of computing system 110. For example, memory controller 118 may control communication between processor 114, system memory 116, and I/O controller 120 via communication infrastructure 112.

I/O controller 120 generally represents any type or form of module capable of coordinating and/or controlling the input and output functions of a computing device. For example, I/O controller 120 may control or facilitate transfer of data between one or more elements of computing system 110, such as processor 114, system memory 116, communication interface 122, display adapter 126, input interface 130, and storage interface 134.

Communication interface 122 broadly represents any type or form of communication device or adapter capable of facilitating communication between example computing system 110 and one or more additional devices. For example, communication interface 122 may facilitate communication between computing system 110 and a private or public network including additional computing systems. Examples of communication interface 122 include, without limitation, a wired network interface (such as a network interface card), a wireless network interface (such as a wireless network interface card), a modem, and any other suitable interface. In one embodiment, communication interface 122 provides a direct connection to a remote server via a direct link to a network, such as the Internet. Communication interface 122 may also indirectly provide such a connection through any other suitable connection.

Communication interface 122 may also represent a host adapter configured to facilitate communication between computing system 110 and one or more additional network or storage devices via an external bus or communications channel. Examples of host adapters include, without limitation, Small Computer System Interface (SCSI) host adapters, Universal Serial Bus (USB) host adapters, IEEE (Institute of Electrical and Electronics Engineers) 1394 host adapters, Serial Advanced Technology Attachment (SATA) and External SATA (eSATA) host adapters, Advanced Technology Attachment (ATA) and Parallel ATA (PATA) host adapters, Fibre Channel interface adapters, Ethernet adapters, or the like. Communication interface 122 may also allow computing system 110 to engage in distributed or remote computing. For example, communication interface 122 may receive instructions from a remote device or send instructions to a remote device for execution.

As illustrated in FIG. 1, computing system 110 may also include at least one display device 124 coupled to communication infrastructure 112 via a display adapter 126. Display device 124 generally represents any type or form of device capable of visually displaying information forwarded by display adapter 126. Similarly, display adapter 126 generally represents any type or form of device configured to forward graphics, text, and other data for display on display device 124.

As illustrated in FIG. 1, computing system 110 may also include at least one input device 128 coupled to communication infrastructure 112 via an input interface 130. Input device 128 generally represents any type or form of input device capable of providing input, either computer- or human-generated, to computing system 110. Examples of input device 128 include, without limitation, a keyboard, a pointing device, a speech recognition device, or any other input device.

As illustrated in FIG. 1, computing system 110 may also include a primary storage device 132 and a backup storage device 133 coupled to communication infrastructure 112 via a storage interface 134. Storage devices 132 and 133 generally represent any type or form of storage device or medium capable of storing data and/or other computer-readable instructions. For example, storage devices 132 and 133 may be a magnetic disk drive (e.g., a so-called hard drive), a floppy disk drive, a magnetic tape drive, an optical disk drive, a flash drive, or the like. Storage interface 134 generally represents any type or form of interface or device for transferring data between storage devices 132 and 133 and other components of computing system 110.

In one example, databases 140 may be stored in primary storage device 132. Databases 140 may represent portions of a single database or computing device or it may represent multiple databases or computing devices. For example, databases 140 may represent (be stored on) a portion of computing system 110 and/or portions of example network architecture 200 in FIG. 2 (below). Alternatively, databases 140 may represent (be stored on) one or more physically separate devices capable of being accessed by a computing device, such as computing system 110 and/or portions of network architecture 200.

Continuing with reference to FIG. 1, storage devices 132 and 133 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 132 and 133 may also include other similar structures or devices for allowing computer software, data, or other computer-readable instructions to be loaded into computing system 110. For example, storage devices 132 and 133 may be configured to read and write software, data, or other computer-readable information. Storage devices 132 and 133 may also be a part of computing system 110 or may be separate devices accessed through other interface systems.

Many other devices or subsystems may be connected to computing system 110. Conversely, all of the components and devices illustrated in FIG. 1 need not be present to practice the embodiments described herein. The devices and subsystems referenced above may also be interconnected in different ways from that shown in FIG. 1. Computing system 110 may also employ any number of software, firmware, and/or hardware configurations. For example, the example embodiments disclosed herein may be encoded as a computer program (also referred to as computer software, software applications, computer-readable instructions, or computer control logic) on a computer-readable medium.

The computer-readable medium containing the computer program may be loaded into computing system 110. All or a portion of the computer program stored on the computer-readable medium may then be stored in system memory 116 and/or various portions of storage devices 132 and 133. When executed by processor 114, a computer program loaded into computing system 110 may cause processor 114 to perform and/or be a means for performing the functions of the example embodiments described and/or illustrated herein. Additionally or alternatively, the example embodiments described and/or illustrated herein may be implemented in firmware and/or hardware.

Methods and Apparatus for Performing Dynamic Respiratory Classification and Tracking I. Ventilatory Threshold (VT) and Respiratory Compensation Threshold (RCT) Determination Broadly, one embodiment of the present invention provides a mobile device application that uses a microphone as a means for recording the user's breathing for the purpose of measuring the VT and RCT thresholds. The microphone can periodically listen to breath sounds at the nose and/or the mouth and the software automatically derives estimates of VT and RCT therefrom. The mobile application may include one or more computer implemented procedures that can record breath sounds and receive pulse rate information from the user to generate an estimate of VT and RCT.

An electronic device, such as a portable computer, mobile electronic device, or a smartphone, may be configured with appropriate software and inputs to permit breath sound data recording and recording data from a heart rate monitor simultaneously. The electronic device, in one embodiment, may be implemented using a computing system similar to computing system 110.

Figure 2:
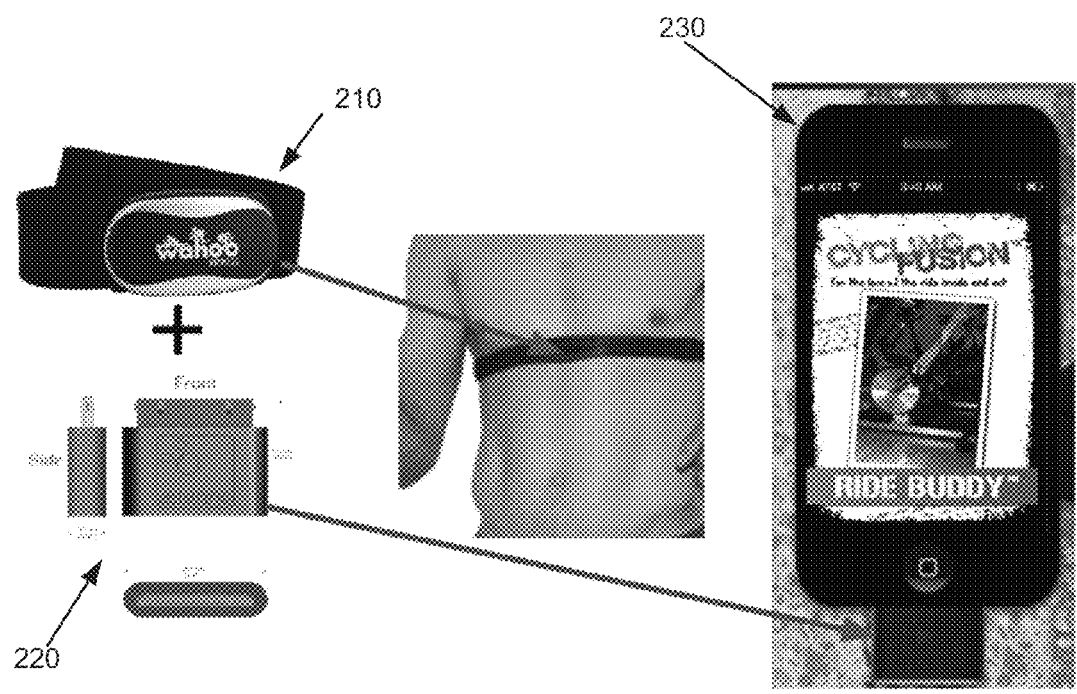
FIG. 2 shows one example of a pulse measuring device for a mobile electronic device according to an exemplary embodiment of the present invention.

FIG. 2 shows one example of a pulse measuring device for a mobile electronic device according to an exemplary embodiment of the present invention. The pulse measuring device shown in the embodiment illustrated in FIG. 2 is a heart monitor transmitter belt 210 that is communicatively coupled with a receiver module 220. The transmitter 210 transmits heart rate information, among other things, to the receiver module 220. In one embodiment, the transmission can take place wirelessly using a near field communication protocol such as Bluetooth. The receiver module 220, in one embodiment, can plug into a portable electronic device 230 such as a smart-phone. The portable electronic device 230, in one embodiment, can use the information from the receiver module 220 to undertake further analysis of the pulse rate. Also it can use the pulse rate in conjunction with the breath sound to generate an estimate of the VT and RCT.

Figure 3:
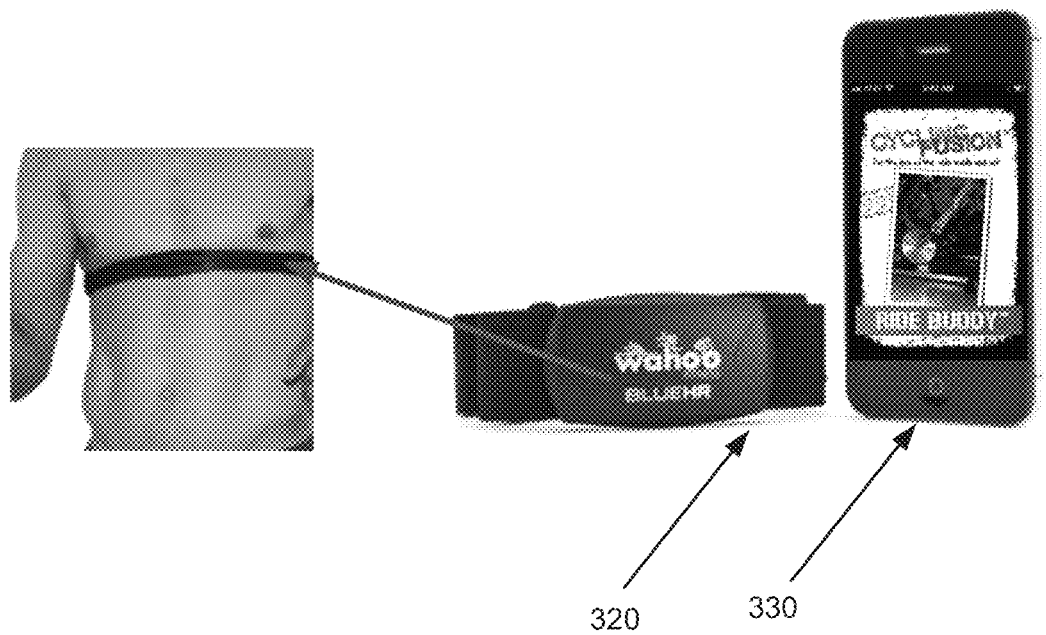
FIG. 3 shows another example of a pulse measuring device for a mobile electronic device according to an exemplary embodiment of the present invention.

FIG. 3 shows another example of a pulse measuring device for a mobile electronic device according to an exemplary embodiment of the present invention. In the embodiment illustrated in FIG. 3, the heart monitor transmitter belt 320 is configured to transmit signals directly to an electronic device 330, such as a smart-phone. The computer-implemented procedures running on device 330 can decode the transmission to undertake further analysis of the pulse rate. Also they can use the pulse rate correlated to the VT and RCT estimates from the breath sound analysis to create heart training zones for the user. In one embodiment, the transmission can take place wirelessly using a near field communication protocol such as Bluetooth. Alternatively, in one embodiment, electronic device 330 can be at a remote location and receive the transmission through a cellular signal.

A microphone can pick up the breathing patterns of the user at rest and during exercise (or some anabolic activity) and a heart monitor transmitter belt, or some other heart rate monitoring device, can simultaneously pick up the heart beats and send them in a continuous (regular frequency) fashion to a heart monitor receiver. In one embodiment, the microphone is readily available commercially and affordable.

Figure 4:
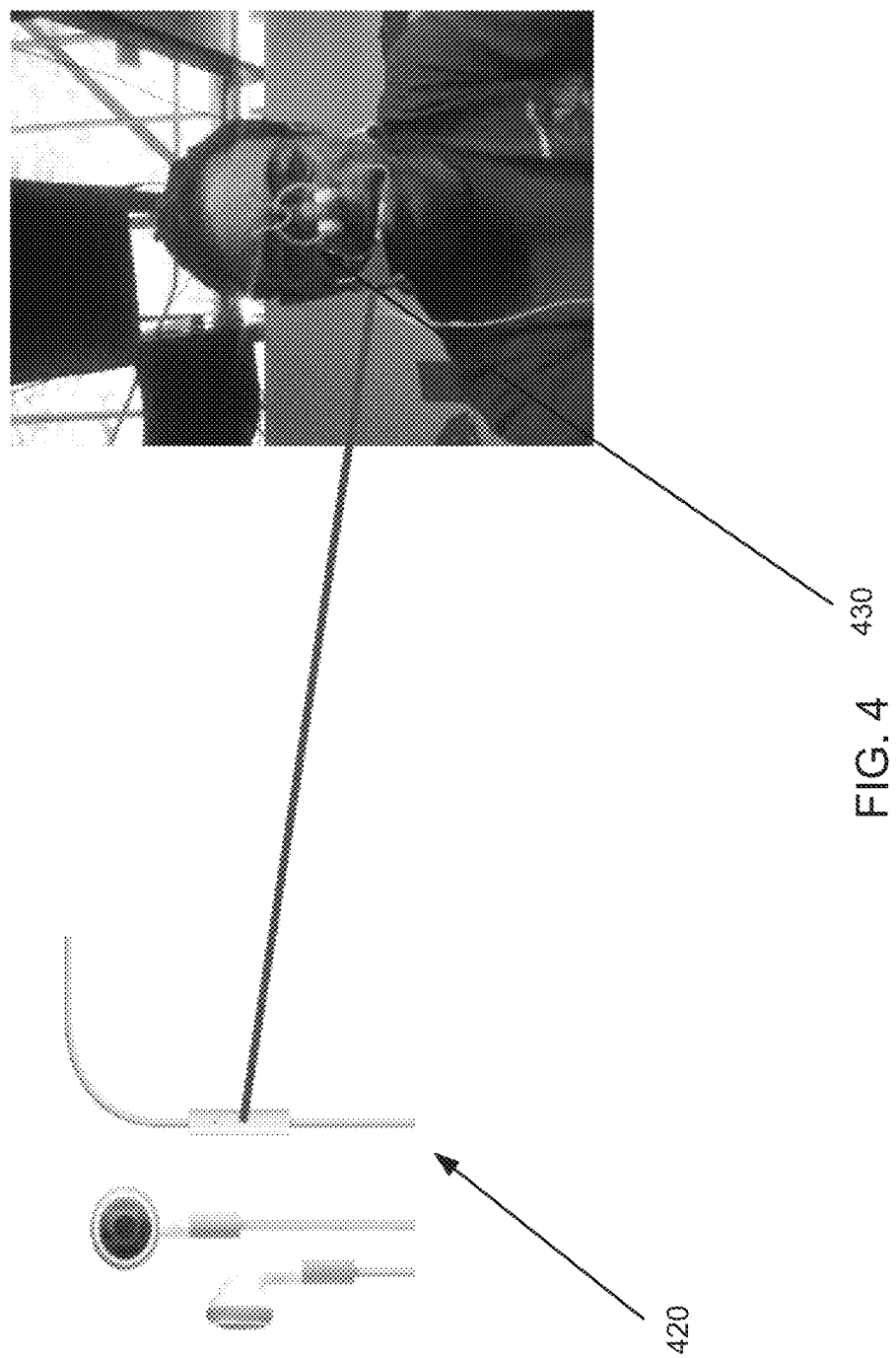
FIG. 4 shows an exemplary breathing microphone set-up used in the methods and apparatus of the present invention.

FIG. 4 shows an exemplary breathing microphone set-up used in the methods and apparatus of the present invention. In one embodiment, a conventional microphone 420, available commercially, can be used to record the breathing patterns of the user. By using only the microphone 420 that comes with many electronic devices (such as an iPad® or iPhone®) and the software as described herewithin, the present invention can provide VT and RCT data for a fraction of the cost of alternative options. Moreover, the test can be self-administered, not requiring special testing equipment or trained personnel.

Various designs may be used to create an accurate breath sound measurement. In some embodiments, as shown in FIG. 4, the user's nose may be closed to ensure the microphone 430 at the user's mouth captures the entirety of the user's breathing. In a different embodiment, the breathing sound can be captured both at the user's nose and the mouth.

Figure 5:
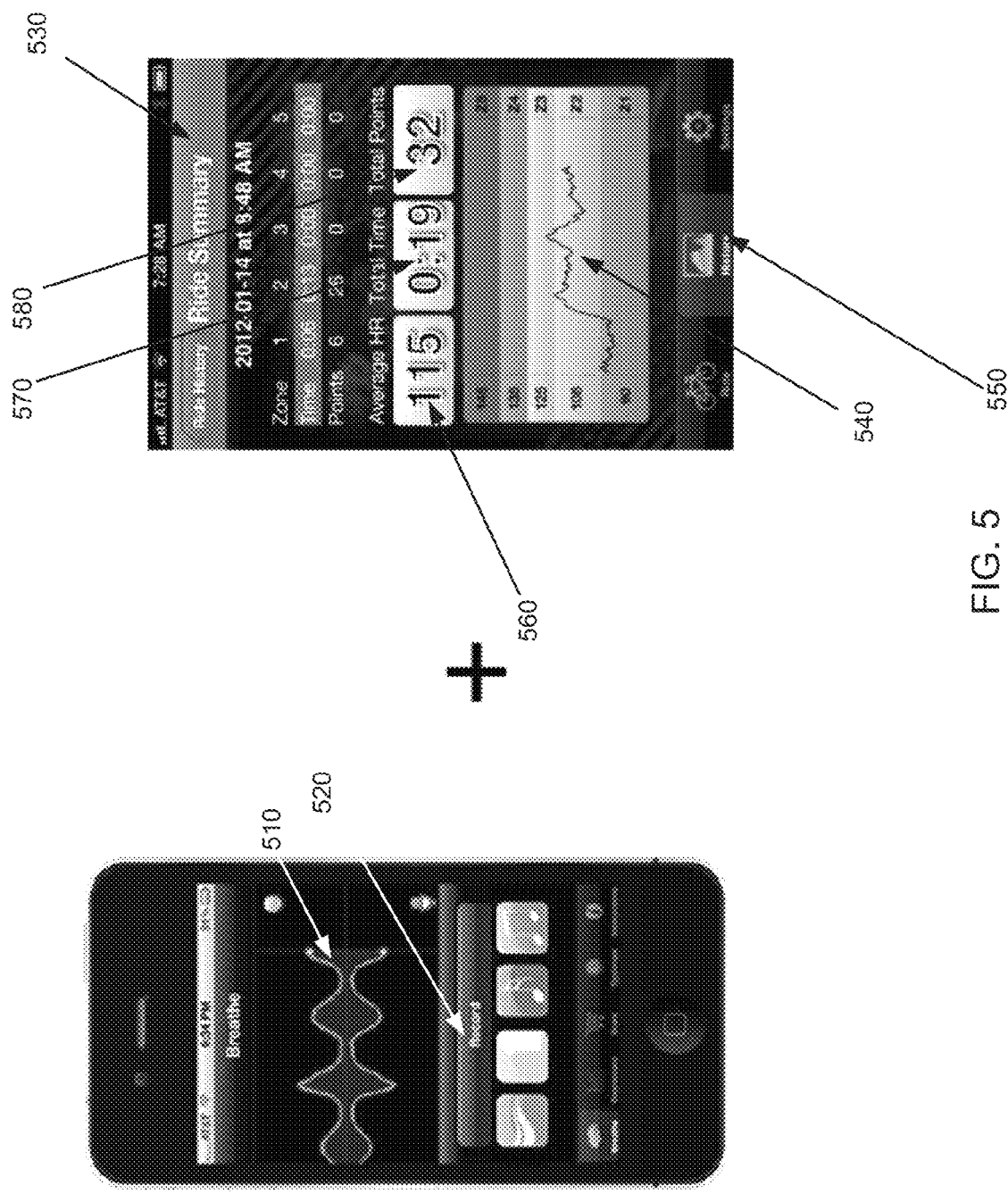
FIG. 5 shows electronic apparatus running software to determine VT and RCT according to an exemplary embodiment of the present invention.

FIG. 5 shows electronic apparatus running software to determine VT and RCT according to an exemplary embodiment of the present invention.

The software can both display the breathing patterns 510 and/or heart rate values 540 on the display screen of the electronic device. It can also save the heart rates, the breathing patterns and all of its related information contained in the users breathing onto the storage medium contained in the electronic device, computer or mobile device. In one embodiment, the user can be provided with an option to start recording the breathing pattern at the click of a push-button 520.

The software can then analyze the information obtained through the breathing sound measurements in order to determine the associated ventilatory (VT) and respiratory compensation (RCT) thresholds and their respective heart rate values from the heart monitor receiver. Research can be conducted to develop a relationship between breathing patterns and VT/RCT ratio. With this information, the software may be programmed with these relationships to provide an accurate estimate of the user's VT and RCT.

The software may be written in one or more computer programming codes and may be stored on a computer readable media. The software may include program code adapted to perform the various method steps as herein described.

The software could be used by itself to analyze any saved audio file that might have been taken from any recording device other than the electronic device having the microphone. If the user had a time line with heart rate values that corresponded to the saved audio file, they could use the software by itself to produce the intended result of the invention.

To use the embodiment of the invention illustrated in FIG. 2, a person would set up the electronic device 230 near the user who is exercising (typically on a stationary bike or a treadmill). They would have the user put a heart monitor 210 on their body, plug the heart monitor receiver 220 into the electronic device, and then begin the recording session by telling the software that the test has begun.

In one embodiment, the software can also collect and save information regarding the user's workout program. As shown in FIG. 5, for example, the software could display the user's ride summary 530 after the user is done exercising on a stationary bike. The user can access the ride summary after the ride by clicking on a "History" tab 550. The display under the "History" tab of the software can be programmed to show the user's average heart rate 560, the total time of the workout 570 and total points 580 accumulated by the user. The display can also be configured to show a graphical display 540 of the user's heart rate.

Once the user confirms that the test is complete, the software can perform the required analysis to determine ventilatory (VT) and respiratory compensation (RCT) thresholds and their related heart rates in Beats Per Minute (BPM).

Embodiments of the present invention could be used in the medical field or any field where ventilatory (VT) and respiratory compensation (RCT) thresholds are used to train athletes or diagnose medical conditions.

II. Dynamic Respiratory Classifier and Tracker (DRCT)

Embodiments of the present invention also provide a method and apparatus for performing respiratory acoustic analysis that uses inexpensive and readily available means for recording breathing sounds e.g. commercially available low-cost microphones. By comparison, conventional approaches require specialized sensors, tracheal or contact microphones, piezoelectric sensors etc.

Further, embodiments of the present invention provide a method and apparatus that takes into account full breath cycles. For example, the present invention can, in one embodiment, detect and separate the phases of the breath with exact timing, limits, etc.

In one embodiment, the present invention is a method and apparatus for dynamically classifying, analyzing, and tracking respiratory activity or human breathing. The present invention, in this embodiment, is aimed at the dynamic classification of a breathing session that includes breath phase and breath cycle analysis with the calculation of a set of metrics that help to characterize an individual's breathing pattern at rest. The analysis is based on audio processing of the breath signal. The audio serves as the main input source and all the extracted results, including the individual breath phase detection and analysis, are based on a series of procedures and calculations that are applied to the source audio input.

In one embodiment, the present invention detects and analyzes audio-extracted breath sounds from a full breath cycle, recognizing the different breath phases (inhale, transition, exhale, rest), detecting characteristics about the breath phases and the breath cycle such as inhale, pause, exhale, rest duration, the wheeze source and type (source of the constriction causing the wheeze can be either nasal or tracheal and the type of the constrictions can be either tension or wheezing) and cough type and source, choppiness and smoothness, attack and decay, etc. These breath cycle characteristics are obtained from the extraction of different audio descriptors from a respiratory audio signal and the performance of audio signal analysis on the descriptors.

In one embodiment, the present invention performs breath pattern statistical analysis on how the characteristics of the breath cycles of a recorded breath session fluctuate over time. For example, applying the mean and variance to breath phase and breath cycle durations, intensity, wheeze source and type, etc. to derive for example, the average respiratory rate, intensity, airway tension level, etc. and also to note when changes occur.

In one embodiment, the present invention provides metrics that are meaningful to user about breath pattern quality including respiratory rate, depth, tension, nasal and tracheal wheeze, pre-apnea and apnea, ramp (acceleration and deceleration), flow (choppiness or smoothness), variability, inhale/exhale ratios, time stamps for reach breath phase with other ratios, etc. by transforming and/or combining breath cycle characteristics and statistics. Metrics can come directly from breath cycle characteristics and statistics transformation and new metrics can be constructed by the combination of more than one characteristic (e.g., where breath phase duration, respiratory rate and breath intensity are used to obtain respiratory depth). Metrics can be provided for one breath cycle or for a number of breath cycles.

The overall procedure responsible for performing the detection and analysis of the audio-extracted breath sounds will be referred to hereinafter as the Dynamic Respiratory Classifier and Tracker ("DRCT").

II.A. Sound Capturing

Figure 6A:
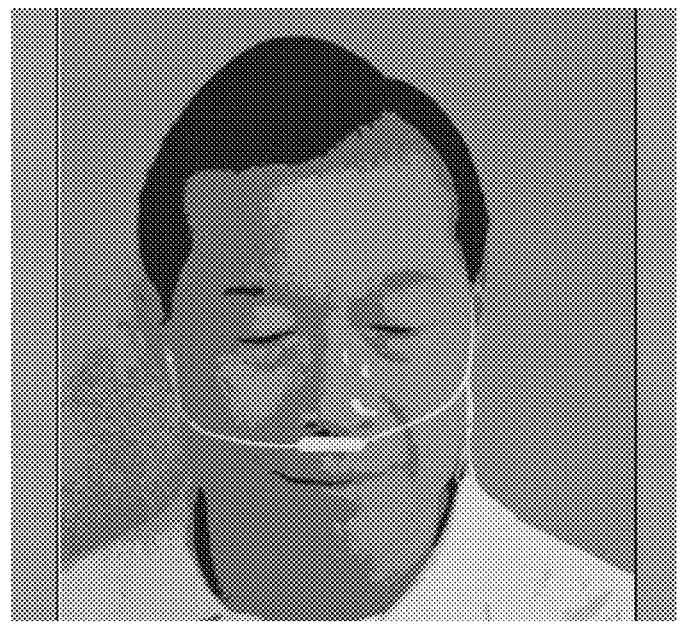
FIG. 6A illustrates an exemplary apparatus comprising a microphone for capturing breathing sounds in accordance with one embodiment of the present invention.

In one embodiment of the present invention, breath sounds are captured by a microphone. FIG. 6A illustrates an exemplary apparatus comprising a microphone for capturing breathing sounds in accordance with an embodiment of the present invention. These breath sounds can be captured at the nose or the mouth or both using an apparatus similar to the one illustrated in FIG. 6A. Further, in one embodiment, the sample rate used is 16 kHz, which is considered to be adequate both for breath phase detection and breath acoustic analysis. However, any sample rate higher than 16 kHz can also adequately be used.

Figure 6B:
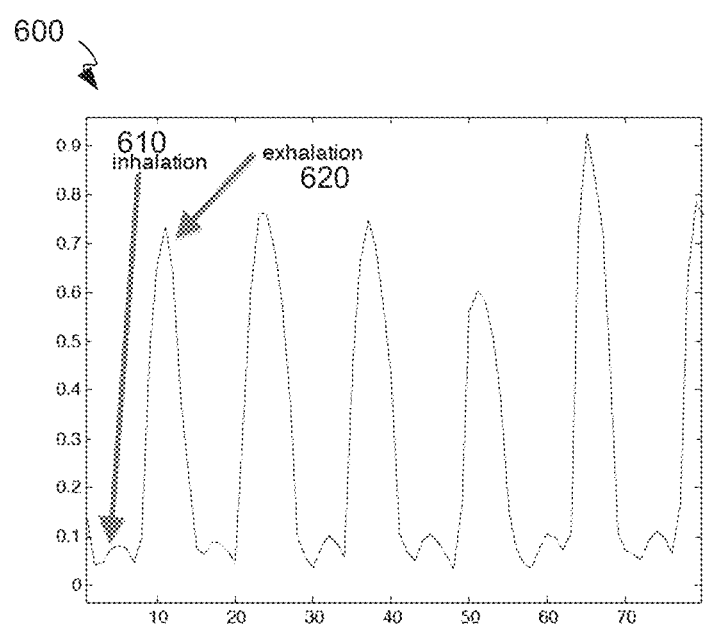
FIG. 6B illustrates an exemplary audio envelope extracted by filtering an input respiratory audio signal through a low-pass filter using an embodiment of the present invention.

The underlying principle that the DRCT procedure is based on is that airflow produces more pressure on the microphone membrane, and thus low frequencies are more apparent during this phase of exhalation. By contrast, higher frequency content is more apparent at the phase of inhalation, since there is no direct air pressure on the membrane. Accordingly, filtering the signal with a low-pass filter will attenuate the inhalation part while leaving the energy of exhalations almost unaffected. The goal of the filtering is typically to create an audio envelope that follows a specified pattern as illustrated in FIG. 6B. FIG. 6B illustrates an exemplary audio envelope 600 extracted by filtering an input respiratory audio signal through a low-pass filter using an embodiment of the present invention. Inhalation lobes 610 should be more attenuated than the exhalation lobes 620 in the envelope.

The DRCT procedure then classifies the lobes into two different classes that correspond to inhalation and exhalation. This classification can provide timestamps for each inhalation and exhalation event and for rest periods to be able to define a full breath cycle with four phases: inhalation, pause or transition, exhalation, and rest. These timestamps can be collected over several breath cycles.

II.B. The DRCT Low Layer Structure

Figure 7:
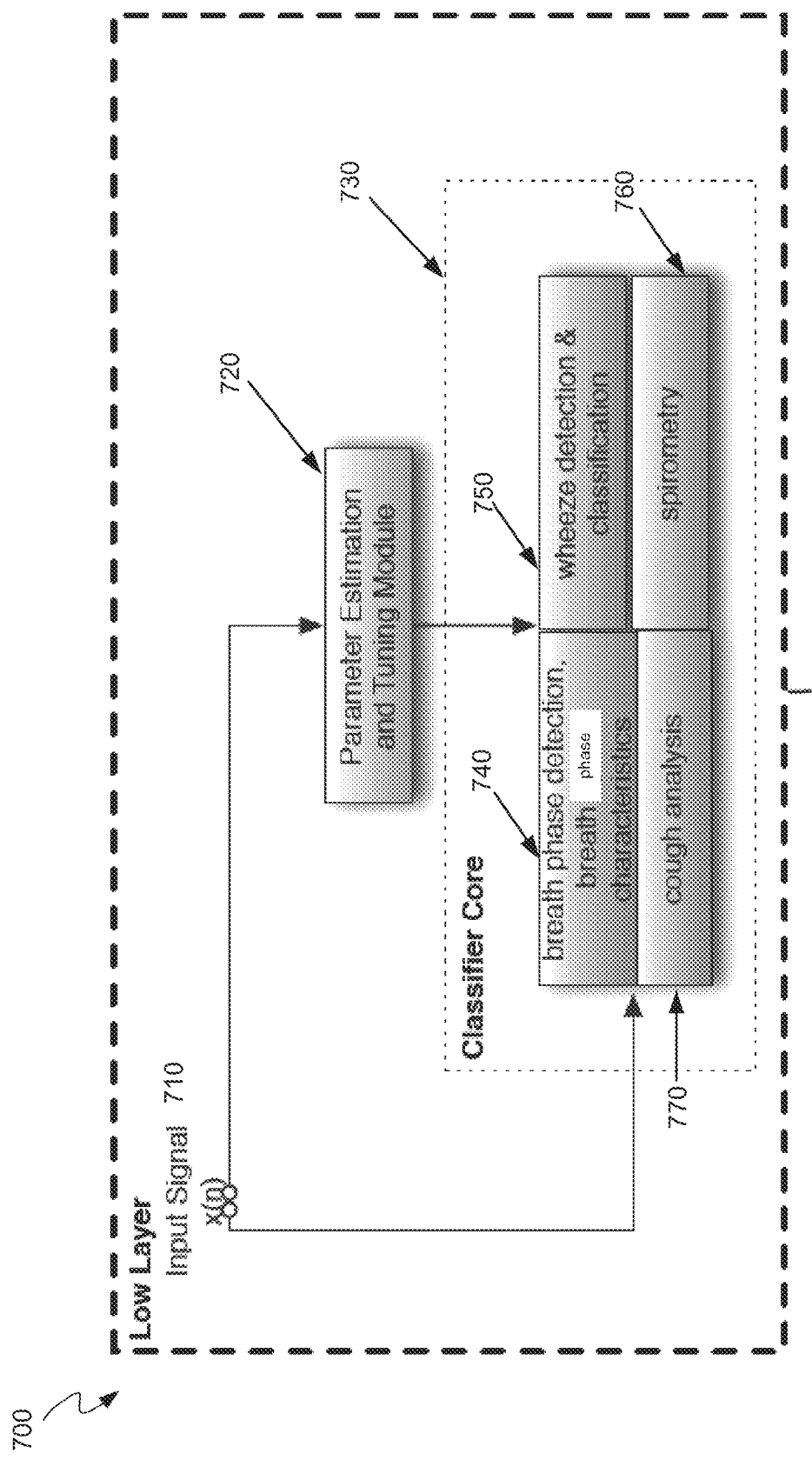
FIG. 7 illustrates a flowchart illustrating the overall structure of the lower layer of the DRCT procedure in accordance with one embodiment of the present invention.

FIG. 7 illustrates a flowchart illustrating the overall structure of the lower layer of the DRCT procedure in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 7 should not be construed as limiting the scope of the invention. Rather, it will be apparent to persons skilled in the relevant art(s) from the teachings provided herein that other functional flows are within the scope and spirit of the present invention. Flowchart 7 may be described with continued reference to exemplary embodiments described above, though the method is not limited to those embodiments.

The DRCT procedure comprises a low layer 700 and a high layer 1500. High layer 1500 will be discussed in connection with FIG. 15.

The low layer comprises a parameter estimation and tuning module 720. Parameter estimation and tuning (PET) module 720 comprises several sub-modules, which collectively shape the signal and its envelope accordingly and extract useful information and statistics that can be used by the sub-modules of the Classifier Core (CC) module 730. Both the PET module 720 and the CC module 730 operate on the input audio respiratory signal 710.

The CC module 730 comprises sub-modules that perform the annotation procedure responsible for classifying the breathing events e.g. wheeze detection etc. In one embodiment, the CC module 730 comprises a breath phase detection and breath phase characteristics module 740, a wheeze detection and classification module 750, a cough analysis module 770 and a spirometry module 760. The CC module 730 and each of its sub-modules will be described in further detailed below.

Figure 8:
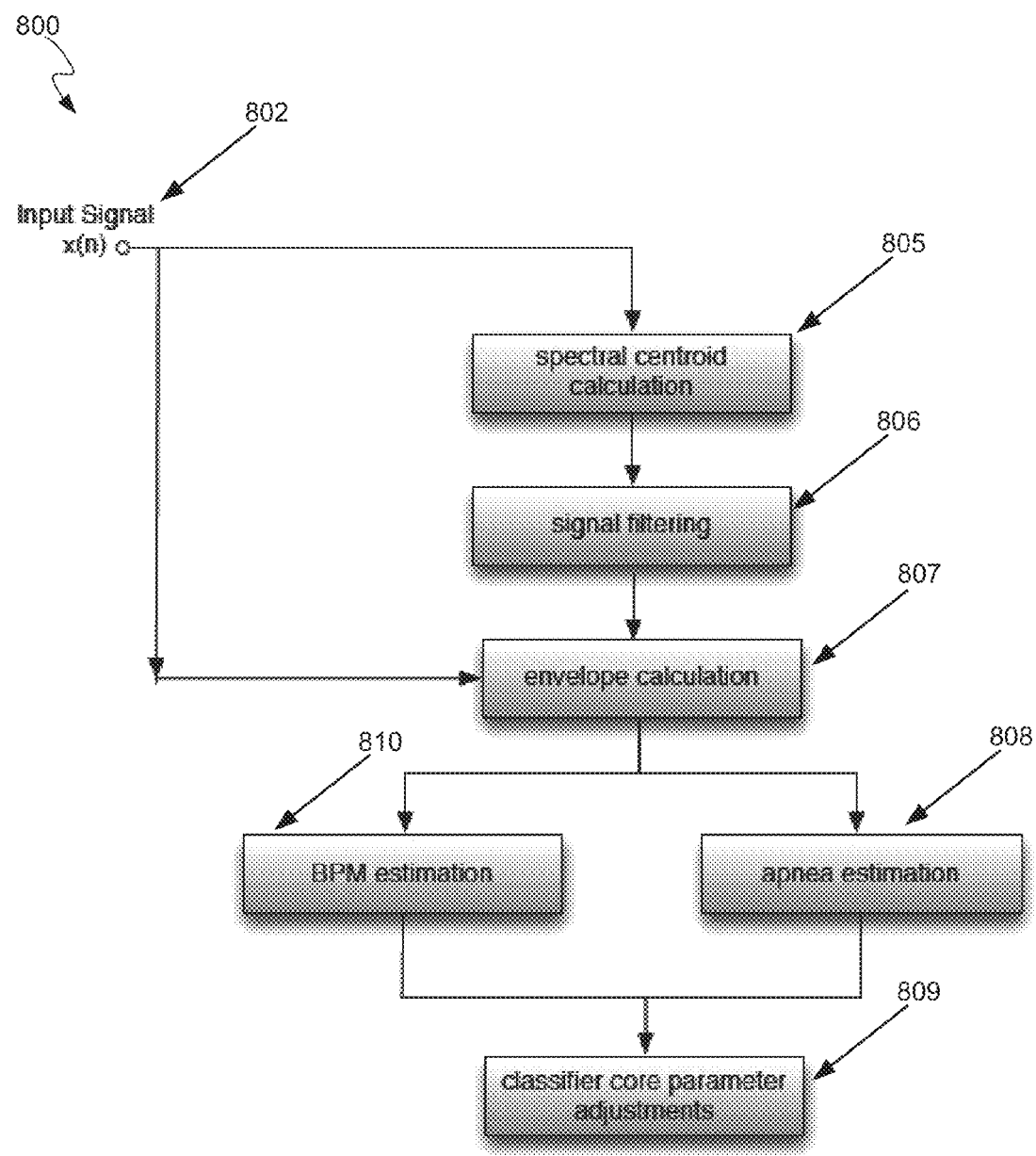
FIG. 8 depicts a flowchart illustrating an exemplary computer-implemented process for implementing the parameter estimation and tuning module shown in FIG. 7 in accordance with one embodiment of the present invention.

FIG. 8 depicts a flowchart 800 illustrating an exemplary computer-implemented process for implementing the parameter estimation and tuning module 720 from FIG. 7 in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 800 should not be construed as limiting the scope of the invention. Rather, it will be apparent to persons skilled in the relevant art(s) from the teachings provided herein that other functional flows are within the scope and spirit of the present invention. Flowchart 800 may be described with continued reference to exemplary embodiments described above, though the method is not limited to those embodiments.

In order to obtain the envelope shape as depicted in FIG. 6, power needs to be subtracted from the higher frequencies that correspond to inhalation sounds. In order to do this, the spectral centroid of each block of the audio input signal 802 needs to be calculated at step 805. The spectral centroid comprises information about the center of gravity of the audio spectrum.

By filtering the signal with a low pass filter tuned to the minimum value of the spectral centroid at step 806, frequencies above the tuning frequency, which usually corresponds to the threshold for inhalation sounds, can be attenuated and, as a result, the desirable envelope shape can be obtained.

At step 807, the envelope calculation is performed. The initial envelope calculation may be performed by using a relatively small window e.g. approximately 60 msec with a 50% overlap. By doing this, all the events that may happen during a breathing cycle e.g. a cough, can be captured and projected in detail. The signals fed into the envelope calculation stage 807 are the input signal and the low passed filtered signal from step 806.

The Breaths Per Minute ("BPM") estimation module 810 (or "respiratory rate" estimation module) analyzes the audio envelope from step 807 and estimates the breaths per minute by employing a sophisticated procedure that analyzes the autocorrelation function of the envelope. BPM estimation is used to adapt the window size that will later be used by the CC module 730. The larger the BPM value, the smaller the window size will likely be, in order to separate events that are close in time.

When the audio envelope is extracted in step 807, the periodicities of its pattern need to be determined in order to estimate the BPM value. To achieve this, the autocorrelation function (ACF) of the envelope is first calculated. The peak of the ACF indicates the period of the pattern repetition. Accordingly, the ACF can provide an estimation of the respiratory rate or BPM.

However, occasionally, environmental noises (usually sudden and unexpected audio events such as a cough) may distort the desirable shape of the ACF. As a result, choosing the highest peak value as a reference for BPM may provide a wrong estimation. Treating the ACF as a dataset, and finding the periodicity from this dataset can address this. In one embodiment, this is done by performing a FFT (Fast Fourier Transform) procedure of an oversampled by 8× and linearly interpolated ACF dataset. Oversampling increases the accuracy since the ACF data can be short. The estimated BPM is given by the location of the highest peak of the magnitude spectrum of the FFT of the oversampled ACF vector.

At step 808, apnea estimation is performed. Long pauses after exhalation are typically characteristic of a breath pattern commonly referred to as apnea. The overall BPM value is smaller in magnitude, thereby, indicating a large window size. The inhalations and exhalations are spaced differently in relation to the overall breath cycle duration and can affect the envelope calculation. Inhalations are very close to exhalations and in order to separate them, a smaller window size is needed in order to attain more precision in the temporal analysis of each breath phase. In particular, the apnea estimation module uses a threshold to detect the duration of silence in a breath signal. For example, if the duration of total silence is larger than the 30% threshold of the total signal duration, then the breath sample being examined may be classified as apnea or pre-apnea.

Finally, at step 809, the classifier code parameter adjustments module initializes and tunes the breath CC module 730 according to the parameters calculated by the PET module 720.

The parameters from the PET module 720 are inputted into the CC module 730 as shown in FIG. 7. The CC module 730 comprises, among other things, the breath phase detection and breath phase characteristics (hereinafter referred to as "BPD") module 740. The BPD module performs signal annotation and classification of the different breath phases and will be explained in further detail in connection with FIG. 9 below. An efficient procedure is employed in the BPD module to distinguish between signal presence and silence (breath rest or pause). Further, the BPD module can also efficiently discriminate between inhalation and exhalation.

The wheeze detection and classification (WDC) module 750 analyzes the input signal and detects wheezing. Wheezing typically comprises harmonic content. The WDC module 750 can be typically configured to be more robust and insensitive to environmental sounds that are harmonic with the exception of sounds that match several qualities of a wheezing sound e.g. alarm clocks, cell phones ringing etc.

The cough analysis module 770 employs procedures to successfully classify a given cough sample into different cough categories, and to detect possible lung or throat pathology, utilizing the analysis and qualities of the entire breath cycle and breath phases.

Spirometry is the most common of the pulmonary function tests, measuring lung function, specifically the amount (volume) and/or speed (flow) of air that can be inhaled or exhaled. The spirometry module 760 performs a spirometry analysis that can be performed on a single forced breath sample by using a set of extracted descriptors such as attack time, decay time, temporal centroid, and overall intensity.

Figure 9:
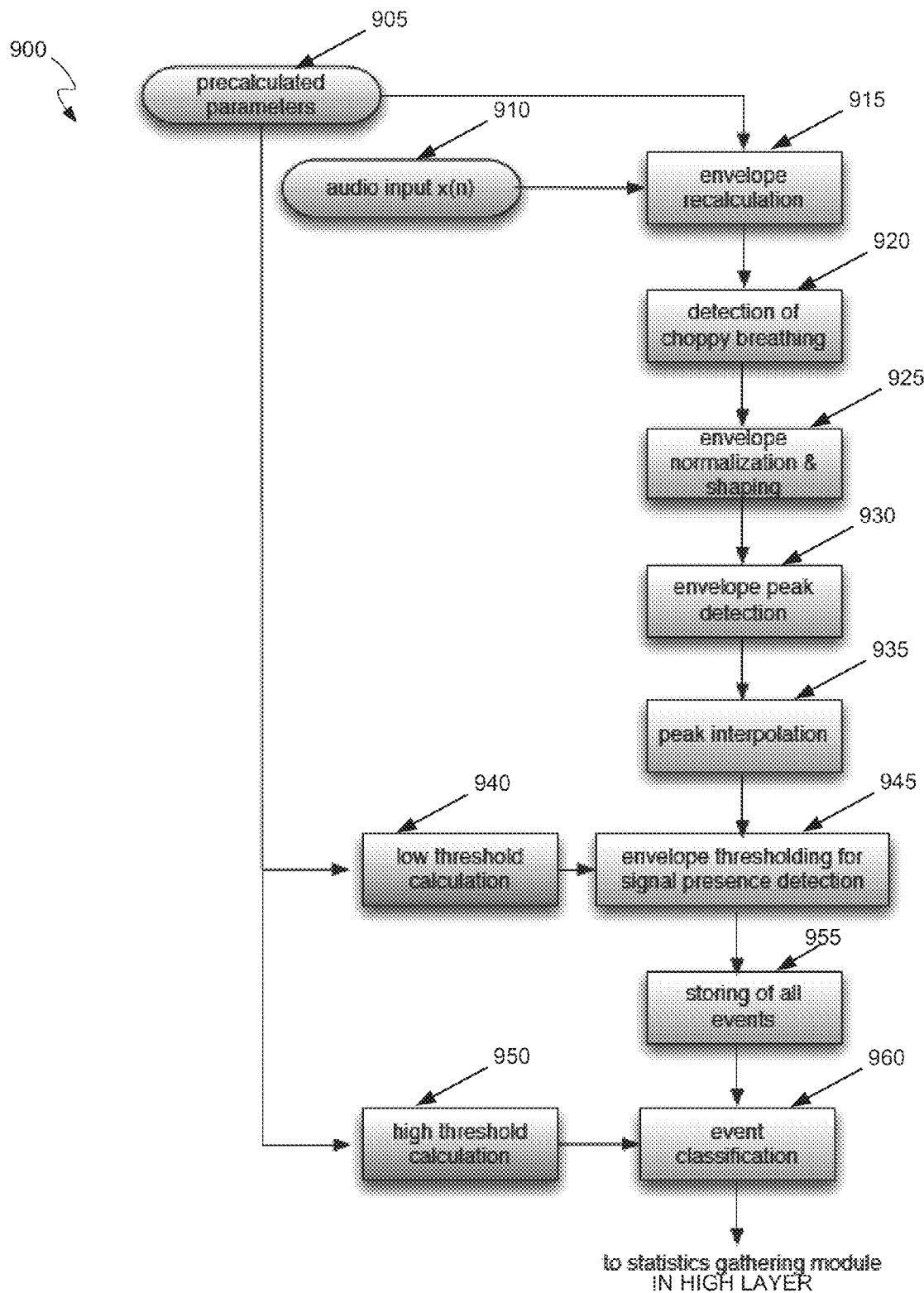
FIG. 9 depicts a flowchart illustrating an exemplary computer-implemented process for the breath phase detection and breath phase characteristics module (the BPD module) shown in FIG. 7 in accordance with one embodiment of the present invention.

FIG. 9 depicts a flowchart 900 illustrating an exemplary computer-implemented process for the breath phase detection and breath phase characteristics module (the BPD module 740) shown in FIG. 7 in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 900 should not be construed as limiting the scope of the invention. Rather, it will be apparent to persons skilled in the relevant art(s) from the teachings provided herein that other functional flows are within the scope and spirit of the present invention. Flowchart 900 may be described with continued reference to exemplary embodiments described above, though the method is not limited to those embodiments.

The BPD module uses several different submodules that are tuned according to the pre-gathered estimated statistics of the PET module 720. These precalculated parameters 905 along with the input audio signal 910 are used to perform an envelope recalculation at step 915. The envelope recalculation module at step 915 recalculates the envelope using a window which has a size set according to the previously estimated BPM and taking into account the existence of possible apnea. The BPM value provides an indication of how close one breath phase is to another and how accurate the timing needs to be. Typically, a suitable window size will eliminate changes in envelope that do not come from choppy breathing, but rather from sudden and slight microphone placement changes. The placement changes may happen throughout a recording and, consequently, determining an appropriate window setting is important.

At step 920, the BPD module performs a detection for choppy breathing. The slopes of the envelope during a segment corresponding to the current breath phase is examined. The BPD module attempts to determine if more than one convex or concave peak exists during a breath phase. For example, if the inhalation or exhalation has a choppy rather than smooth quality, consecutive inhalations or exhalations are very close to one another. In such a case, the BPD module will merge them under a unique envelope lobe so that they are separated and treated as more than one consecutive breath phase of the same kind. The ability to detect, count, and measure choppy breathing events results in better BPM analysis as well as provides important information about the characteristic and quality of breathing.

At step 925, the BPD module performs envelope normalization and shaping. Further, DC offset removal takes place also. DC typically corresponds to environmental hum noise, thus a type of noise filtering is effectuated.

At step 930, envelope peak detection is performed by the BPD module. The peaks of the envelope, both concave and convex, in order to determine the start and end timestamps of each breath cycle, and to gather the peak values that will be fed into the high threshold calculation module at step 950.

At step 935, a peak interpolation is performed. A new interpolated envelope is created. This new envelope is a filtered envelope version that does not have false peaks created as a result of environmental noise.

A low threshold is then calculated at step 940 and a high threshold is calculated at step 950. The low threshold calculated at step 940 is responsible for detecting signal presence. Accordingly, it detects all events, both inhalations and exhalations. The higher threshold calculated at step 950 is used to discriminate between inhalation and exhalation events. The two thresholds are calculated by using moving average filters on the interpolated envelope. The functional difference between these two filters, in one embodiment, is that for the high threshold determination, the moving average filter uses a variable sample rate since it typically uses envelope peaks as input, whereas for the low threshold determination, the moving average filter uses all the envelope samples.

At step 945, envelope thresholding is performed for signal presence detection. As discussed above, the low threshold is used to detect all the events, while the high threshold is used to discriminate between inhalation and exhalation events.

At step 955, a storing of all detected events takes place and at step 960 the stored events are classified. The information regarding the events is then transmitted for statistics gathering in high layer 1500.

In one embodiment, the CC module 730 also comprises the WDC module 750. In contrast to conventional approaches that use expensive equipment for breath sound capturing and computationally expensive image analysis procedure that detect heavy wheezing by analyzing spectrogram images, the present invention is advantageously able to not only detect wheezing events, but also able to classify them according to their nature as tension or wheezing of different magnitude (from light to heavy), by using a relatively less computationally intensive approach that also performs the analysis in real-time.

The framework for the WDC module 750 is based on a time frequency analysis of the auditory signal. The analysis performed by the WDC module 750 is able to detect periodic patterns in the signal and to classify them according to their spectrum. The premise underlying the analysis that makes wheeze detection possible is that when constrictions occur in several areas of the respiratory system, different kinds of lobes rise in the frequency spectrum as a result of air resonating in the constrictions and cavities that may exist. These lobes are characterized according to their magnitude, location and width by the WDC module 750. Furthermore, the relationship between consecutive spectrums can be useful for constriction classification.

In one embodiment, an important descriptor that helps to determine the nature of the wheezing sound is the amount of change between consecutive spectrums or blocks also called a similarity descriptor. The similarity descriptor is used by the WDC module 750 to determine if an event should be considered. For example, a sudden event that features harmonic content and does not last as long as a wheeze event is ignored. Even if the harmonic pattern comes from the lungs or the vocal tract of the subject, it is not identified as a pathology if it is that short, e.g., less than 2 consecutive blocks that sum up to 200 msec of duration. Also, important to note for purposes of tension classification is that tension tends to produce frequency spectrums richer in high frequencies with wider lobes as the constrictions do not form cavities that would result in distinct frequencies.

Figure 10:
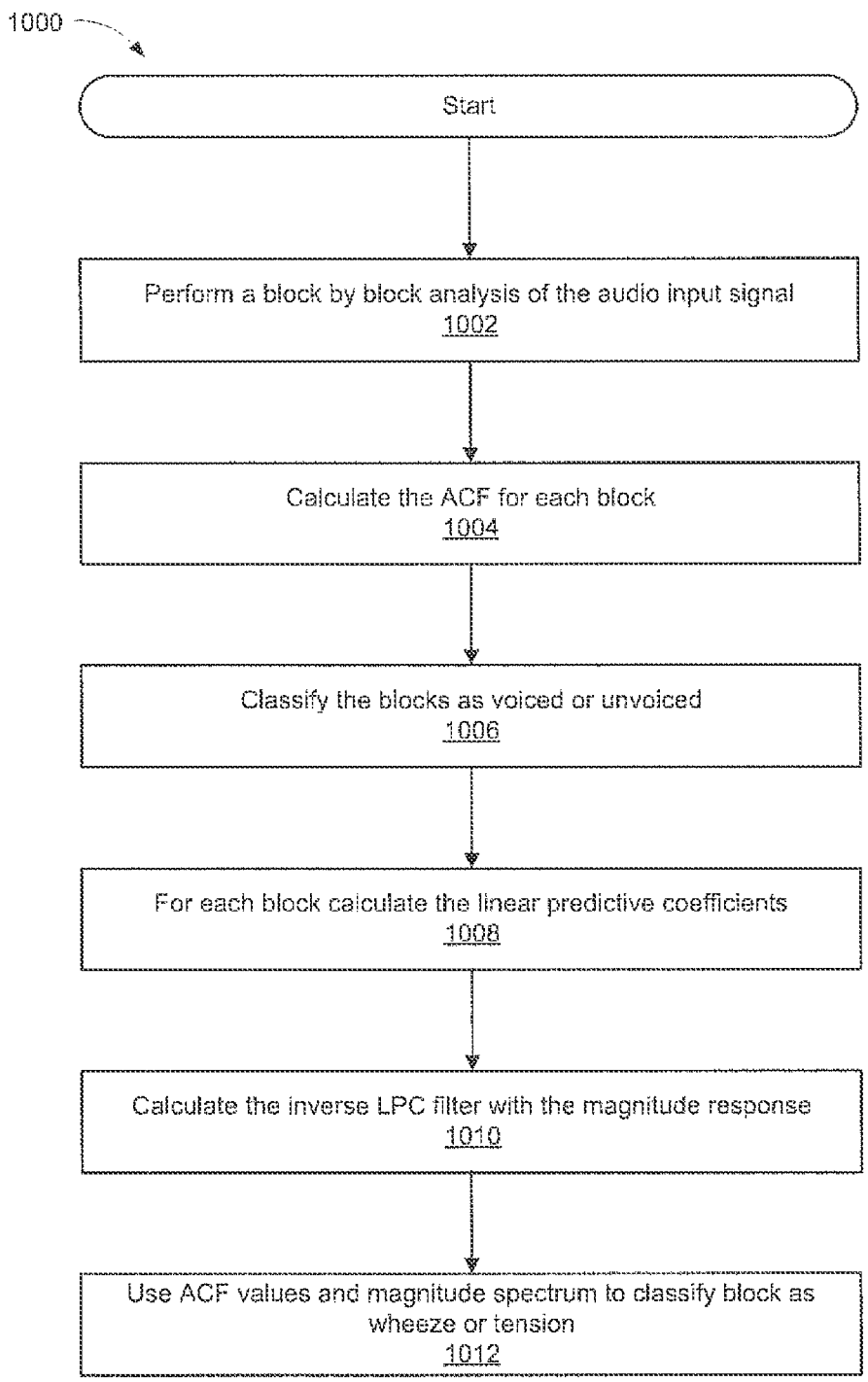
FIG. 10 depicts a flowchart illustrating an exemplary computer-implemented process for the wheeze detection and classification module (WDC module) from FIG. 7 in accordance with one embodiment of the present invention.

FIG. 10 depicts a flowchart 1000 illustrating an exemplary computer-implemented process for the wheeze detection and classification module (WDC module 750) from FIG. 7 in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 1000 should not be construed as limiting the scope of the invention. Rather, it will be apparent to persons skilled in the relevant art(s) from the teachings provided herein that other functional flows are within the scope and spirit of the present invention. Flowchart 1000 may be described with continued reference to exemplary embodiments described above, though the method is not limited to those embodiments In one embodiment, at step 1002, the WDC module 750 performs a block by block analysis of the audio signal 710 with a window which is 2048 samples long (approximately 12 msec for the operating sample rate of 16 Khz) and a 50% overlap factor.

At step 1004, for each block, the ACF is calculated. If the maximum of the normalized ACF of the block under analysis (excluding the first value that corresponds to zero time-lag) is above 0.5, then the block is considered to be "voiced."

By using this information, at step 1006, the WDC module 750 is able to classify the blocks as voiced and unvoiced. By further extension of this procedure, in one embodiment, the WDC module 750 is able to classify even more incoming blocks as clearly voiced, possibly voiced and unvoiced. Typically, a clean breath sound that does not feature any possible harmonic component (and therefore comprises no wheezing at all) should show near noise characteristics, which means that the ACF values will be really low.

Tension in breathing is typically not able to produce clear harmonic patterns. Blocks wherein the maximum value of the normalized ACF is between 0.15-3 will typically be classified as "tension" blocks.

Incoming blocks wherein the maximum value of the normalized ACF is above 0.3 are considered to typically be "voiced" or "wheeze" blocks.

Following this process, in one embodiment, all blocks are processed again for further evaluation. At step 1008, for each block, the linear predictive coding (LPC) coefficients are calculated using the Levinson-Durbin process. Subsequently, at step 1010, the inverse LPC filter is calculated with its magnitude response. The magnitude response is then inspected.

Tension typically produces high frequency content with wide lobes in the magnitude spectrum since the pattern is not clearly harmonic. On the other hand, lobes resulting from wheezing are more narrow and usually occur in lower frequencies in the spectrum.

Figure 11A:
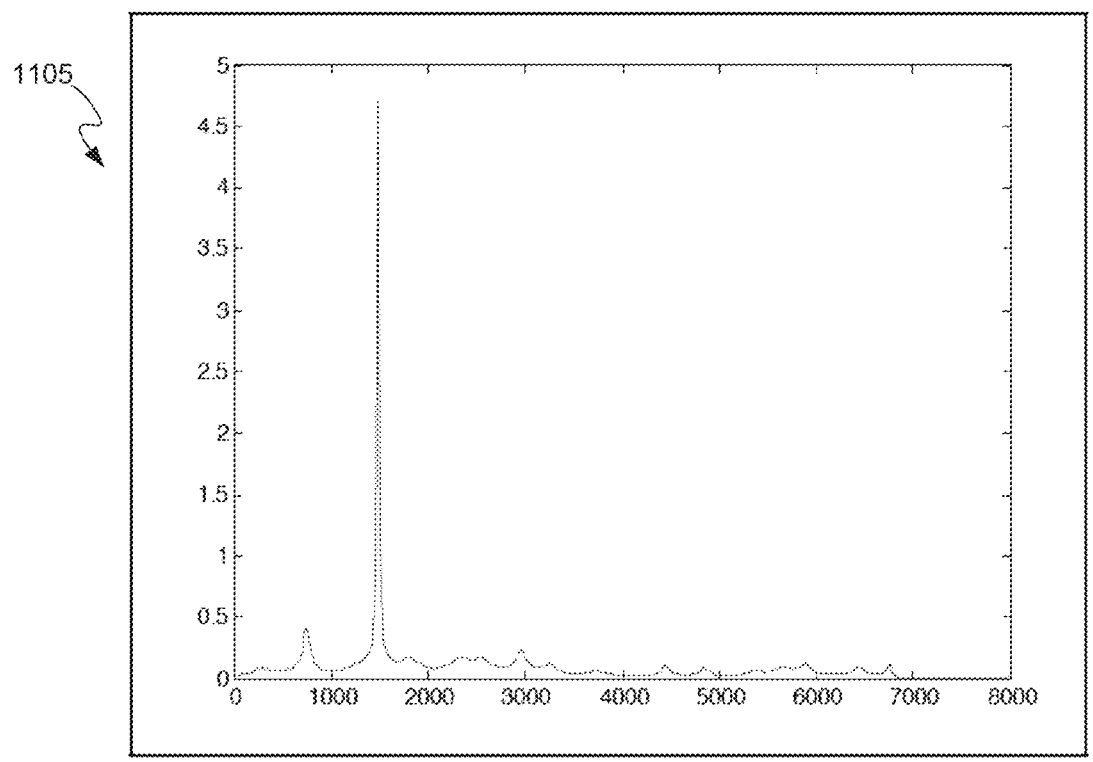
FIG. 11A illustrates a spectral pattern showing pure wheezing.

FIG. 11A illustrates a spectral pattern showing pure wheezing. The WDC module 750 would likely identify spectral pattern 1105 to be associated with wheezing resulting from a single constriction in the trachea because of the single narrow lobe and the lower frequency at which the lobe occurs.

Figure 11B:
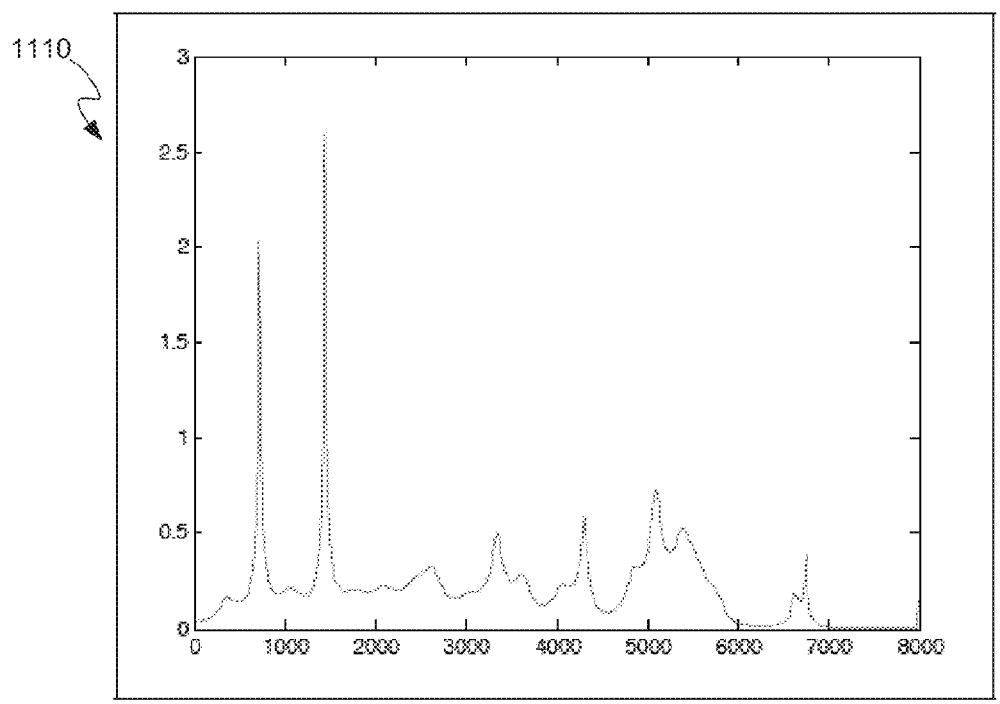
FIG. 11B illustrates a spectral pattern showing wheezing in which more than one constriction is apparent.

FIG. 11B illustrates a spectral pattern showing wheezing in which more than one constriction is apparent. Spectral pattern 1110 illustrates multiple narrow lobes in the lower frequencies that the WDC module 750 will likely identify as wheezing resulting from multiple constrictions in the trachea. The higher frequency content above 3000 Hz in spectral pattern 1110 may also be associated with tension.

Figure 12A:
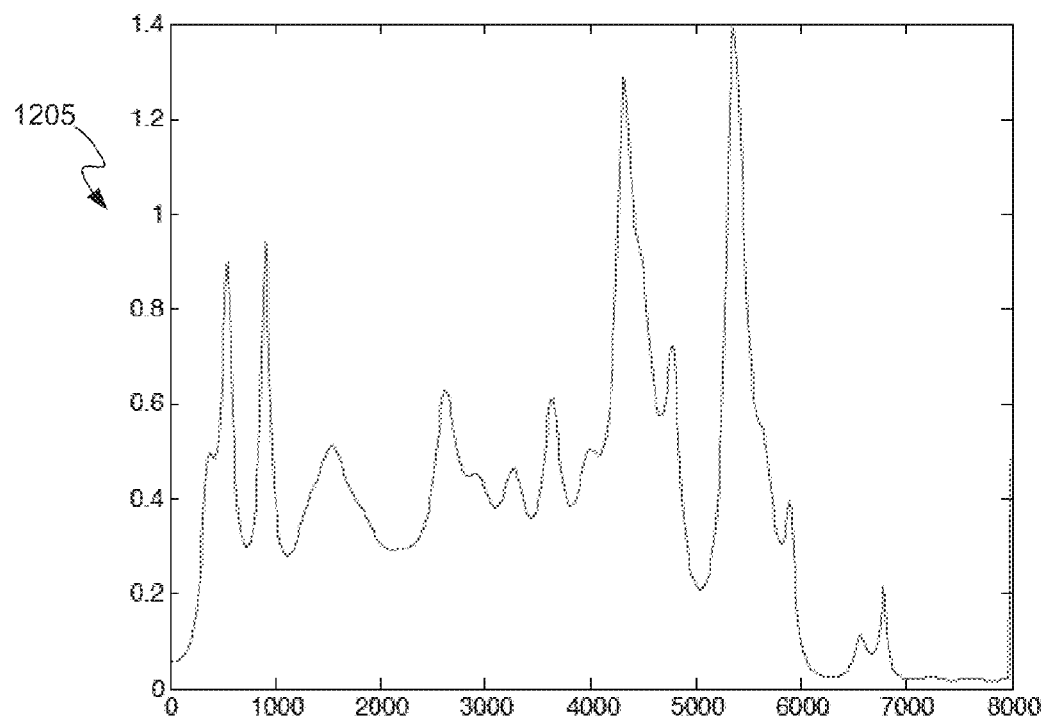
FIG. 12A illustrates a first spectral pattern showing tension created by tracheal constrictions.

FIG. 12A illustrates a first spectral pattern showing tension created by tracheal constrictions. Spectral pattern 1205 illustrates rich frequency content and wide lobes above 3000 Hz, which will likely be identified as tension resulting from multiple tracheal constrictions by the WDC module 750.

Figure 12B:
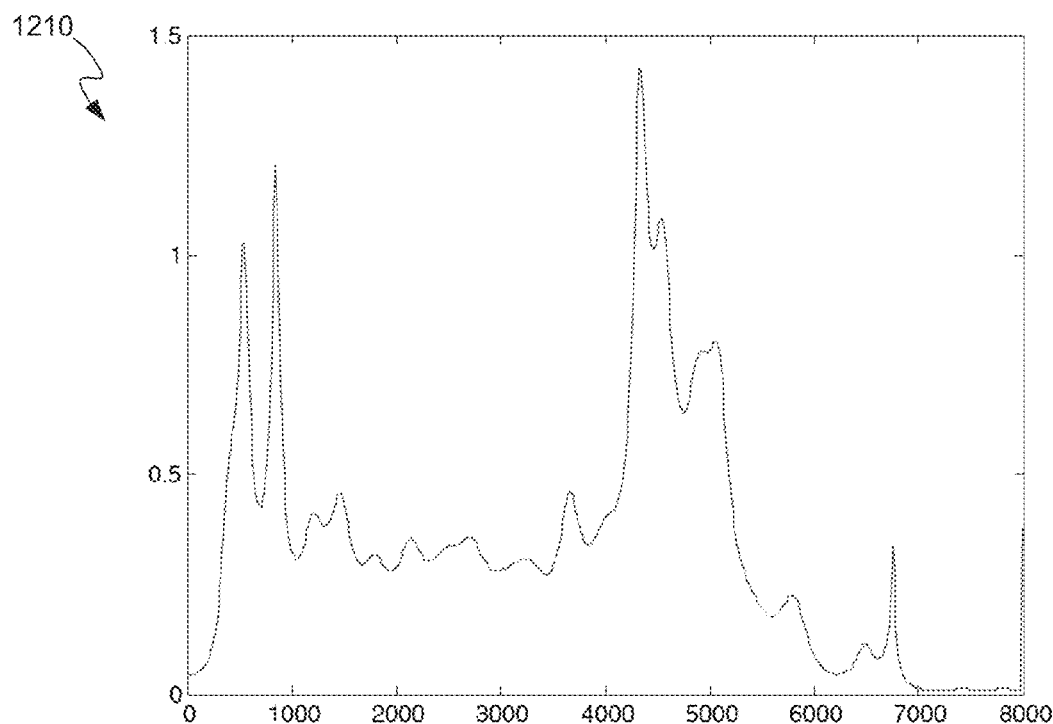
FIG. 12B illustrates a second spectral pattern showing tension created by tracheal constrictions.

FIG. 12B illustrates a second spectral pattern showing tension created by tracheal constrictions. Similar to spectral pattern 1205, spectral pattern 1210 illustrates wide lobes and rich frequency content above 3000 Hz, which will likely be identified as tension resulting from multiple tracheal constrictions by the WDC module 750.

Finally, at step 1012 in FIG. 10, a decision procedure that takes into account maximum ACF values and LPC magnitude spectrum lobe location and width will typically be employed by the WDC module 750 to determine whether the block should be classified as wheeze or tension.

The spectral centroid descriptor may, in one embodiment, be employed as a meter of spectrum gravity towards lower or higher frequencies. In one embodiment, the ratio of the high and low band of the magnitude spectrum may also be examined. A formula that may be used to decide whether to classify a block as wheeze or tension may be the following:

$$n.a.l.w \cdot \left( \alpha \cdot m_{ACF} + (1-\alpha) \frac{B_h}{B_l} \right) \overset{H_0}{\underset{H_1}{\gtrless}} \lambda$$

where $H_0$ corresponds to wheeze, $H_1$ corresponds to tension, n.a.l.w corresponds to normalized average lobe width, $B_h$ corresponds to high band energy, $B_l$ corresponds to low band energy, $\alpha$ is a weight factor, and $\lambda$ is a suitably chosen threshold based on the training set.

In most cases constrictions in the trachea can be complicated. Accordingly, constrictions in the trachea will result in a richer spectrum with more harmonics and fundamental frequencies, each one corresponding a different constriction. By comparison, nasal constrictions produce less frequencies with fewer harmonics. The WDC module 750, in one embodiment, can determine whether the wheeze is nasal or tracheal by counting the number of produced harmonics.

Figure 13A:
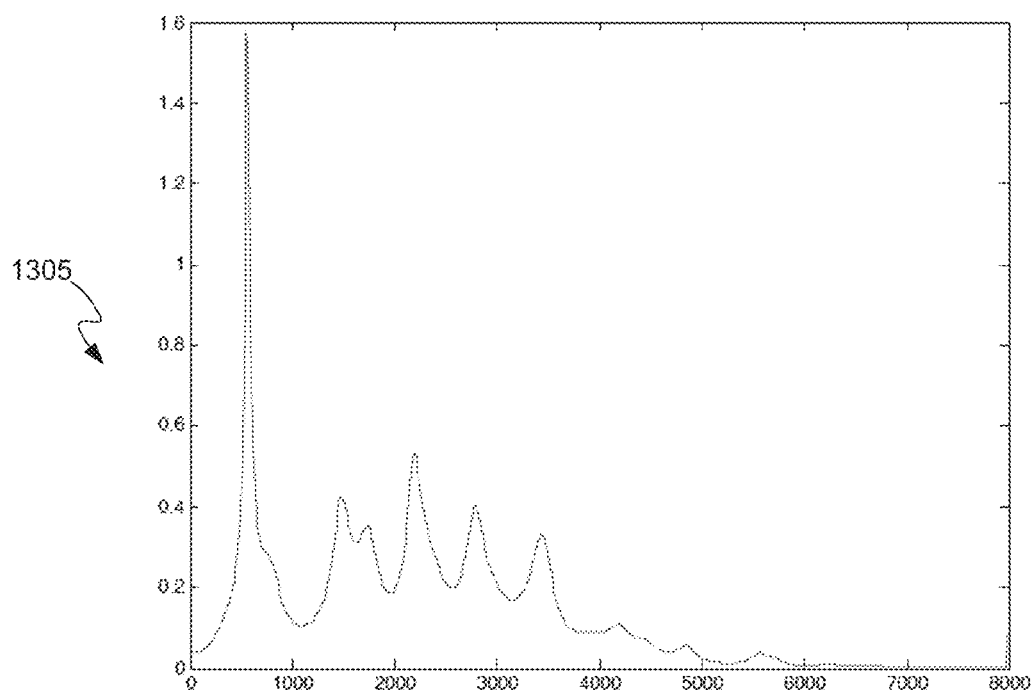
FIG. 13A illustrates a spectral pattern showing wheezing created as a result of nasal constrictions.

FIG. 13A illustrates a spectral pattern showing wheezing created as a result of nasal constrictions. As seen in FIG. 13A, spectral pattern 1305 is characterized by a narrow lobe occurring at a lower frequency value and overall fewer harmonics as compared against FIGS. 11A and 11B. Accordingly, WDC module 750 can identify it as resulting from a wheeze produced due to one or more nasal constrictions.

Figure 13B:
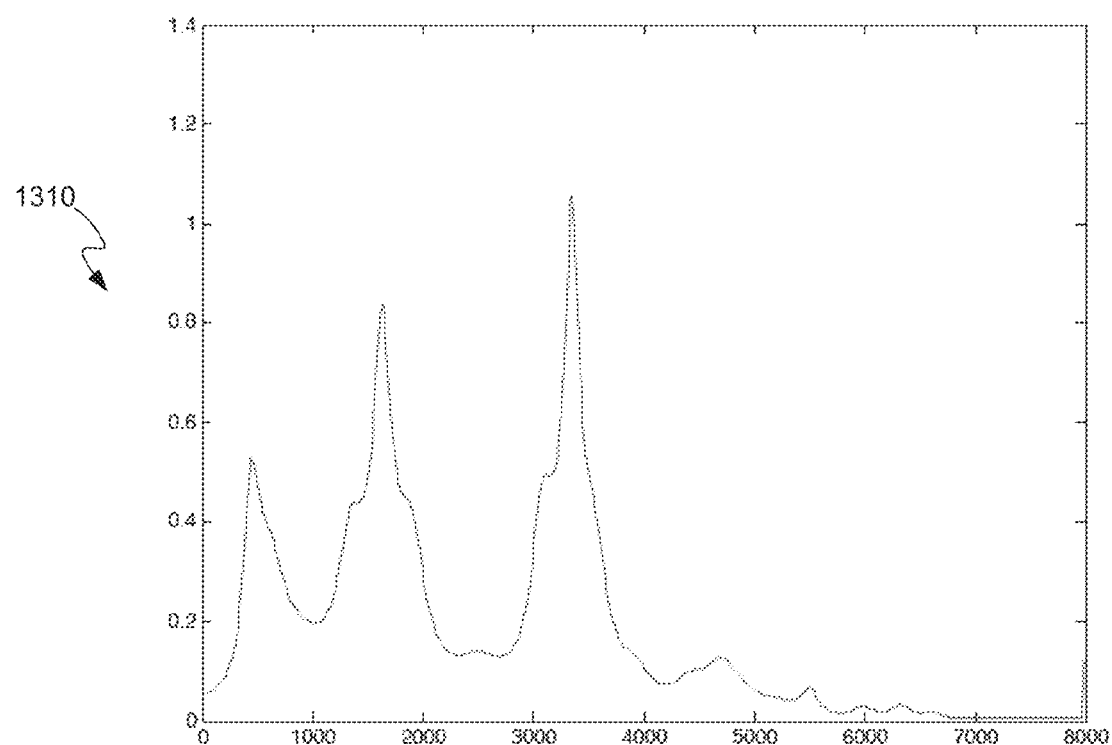
FIG. 13B illustrates a spectral pattern showing tension created as a result of nasal constrictions.

FIG. 13B illustrates a spectral pattern showing tension created as a result of nasal constrictions. As seen in FIG. 13B, spectral pattern 1310 is characterized by wider lobes in the higher frequencies and overall fewer harmonics as compared with FIGS. 12A and 12B. Accordingly, WDC module 750 can identify it as resulting from tension produced due to one or more nasal constrictions.

In one embodiment, the CC module 730 also comprises the cough analysis module 770, which provides a procedure for performing cough analysis. The cough analysis module 770 employs methods in order to successfully classify a given cough sample into different cough categories, and to detect possible lung or throat pathology by utilizing the analysis and qualities of the entire breath cycle and the breath phases.

Coughs can be classified into several different categories. These categories can further be separated into subcategories regarding the cough pattern and the cough's sound properties. Categories based on the cough sound properties include the following: dry cough, wet cough, slow rising, fast rising, slow decay, fast decay. Categories based on the cough pattern can be separate into the following: one shot or repetitive, e.g., barking cough.

Other important properties that can provide important information about the lung and throat health comprise the retrigger time and inhalation quality. Retrigger time is the time it takes for a subject to inhale in order to trigger the next cough in a repetitive pattern. Retrigger time typically indicates how well the respiratory muscles function.

The inhalation quality can be determined by performing a wheeze analysis on the portion of the auditory signal that provides information to indicate if there is respiratory tension or damage. For example, a wheezing analysis on the inhalation before the cough takes place, combined with the analysis of the cough's tail, will generate descriptors that can be used to decide if the cough is a whooping cough.

Furthermore, the cough's sound can be separated into two components: a harmonic one and a noisy one. In whooping cough, subjects find it difficult to inhale and, accordingly, the harmonic part of the sound will rise up faster than the noisy part, which is usually predominant in healthy subjects. The ratio of the harmonic and noisy slopes can be used to determine if a cough is a whooping cough.

Figure 14:
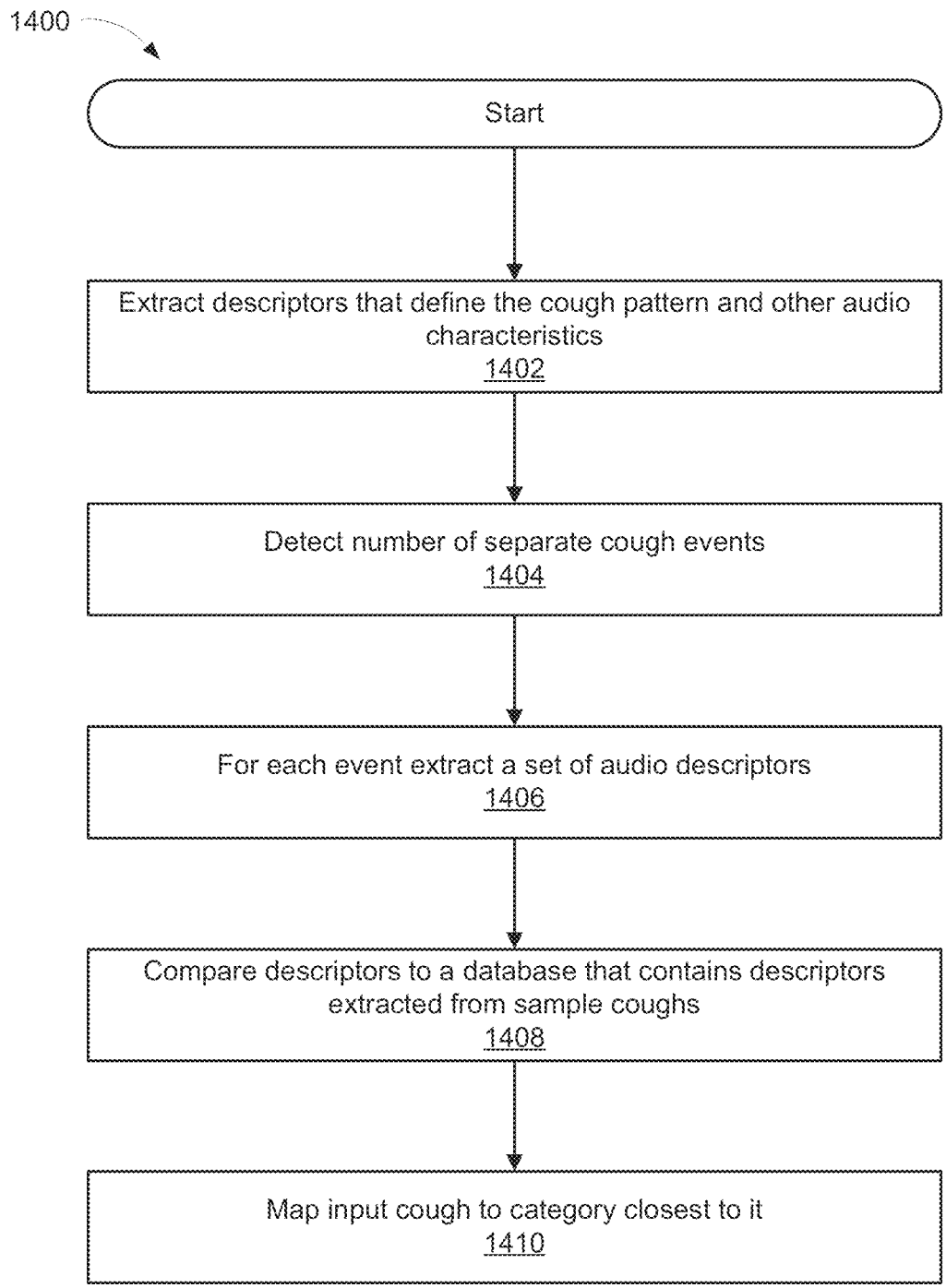
FIG. 14 depicts a flowchart illustrating an exemplary computer-implemented process for the cough analysis module 770 shown in FIG. 7 in accordance with one embodiment of the present invention.

FIG. 14 depicts a flowchart 1400 illustrating an exemplary computer-implemented process for the cough analysis module 770 shown in FIG. 7 in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 1 should not be construed as limiting the scope of the invention. Rather, it will be apparent to persons skilled in the relevant art(s) from the teachings provided herein that other functional flows are within the scope and spirit of the present invention. Flowchart 1400 may be described with continued reference to exemplary embodiments described above, though the method is not limited to those embodiments.

In order to perform cough analysis, at step 1402, the cough analysis module 770 first uses the audio input signal 710 to extract a set of descriptors that will both define the cough's pattern plus other audio characteristics and properties.

At step 1404, the number of separate cough events is detected. If more than one event is detected, for example, then the analysis module 770 must determine if there is a repetitive cough pattern. For each one of the events, at step 1406, a set of audio descriptors is extracted such as attack time, decay time, envelope intensity, spectral centroid, spectral spread, spectral kyrtosis, harmonicity, etc.

At step 1408, these audio descriptors are compared to a database that contains descriptors extracted from sample coughs of the subject. Finally, at step 1410, the input cough is mapped to the category closest to it. In this way the present invention advantageously customizes the cough analysis using the subject's own cough.

A cough can typically be separated into two parts. The attack time part, which is the percussive sound of the cough, and the tail (decay time part). Both of these two parts can be analyzed separately. In one embodiment, a full wheeze analysis can be carried out on the tail to determine pathology related to asthma. Further, the analysis on the percussive part of the cough can be indicative of the condition of the lung tissue and respiratory muscles.

Finally, in one embodiment, the CC module 730 also comprises the spirometry module 760. Spirometry is the most common of the pulmonary function tests, measuring lung function, specifically the amount (volume) and/or speed (flow) of air that can be inhaled or exhaled. Descriptors such as intensity, attack and decay time, combined with wheeze analysis can be used as well for spirometry with an appropriate setting for a microphone installation and a standardized sample database. The analysis is performed on a single forced breath sample typically. The procedure initially extracts a set of descriptors such as attack time, decay time, temporal centroid, and overall intensity. Then the sample is classified into one of the designated categories, which have been pre-defined in terms of their descriptors, using the minimum distance.

II.C. The DRCT High Layer Structure

As discussed above, the DRCT procedure comprises a low layer 700 and a high layer 1500. Once the low-level analysis of the CC module 370 is complete, a set of vectors and arrays containing the results from the direct signal processing is passed on to the high layer 1500 also known as the post-parsing and data write-out layer of the design. This layer performs a number of post-processing operations on the raw data and extracts the final statistics and scores. Further, in one embodiment, it publishes the extracted statistics and scores by performing an XML write-out. The techniques used in post-processing will typically depend on the results from low level 700. Stated differently, the vectors of low-level analysis data from low layer 700 are processed by high layer 1500, mapped to their corresponding detected breath cycles, and statistics are extracted.

Figure 15:
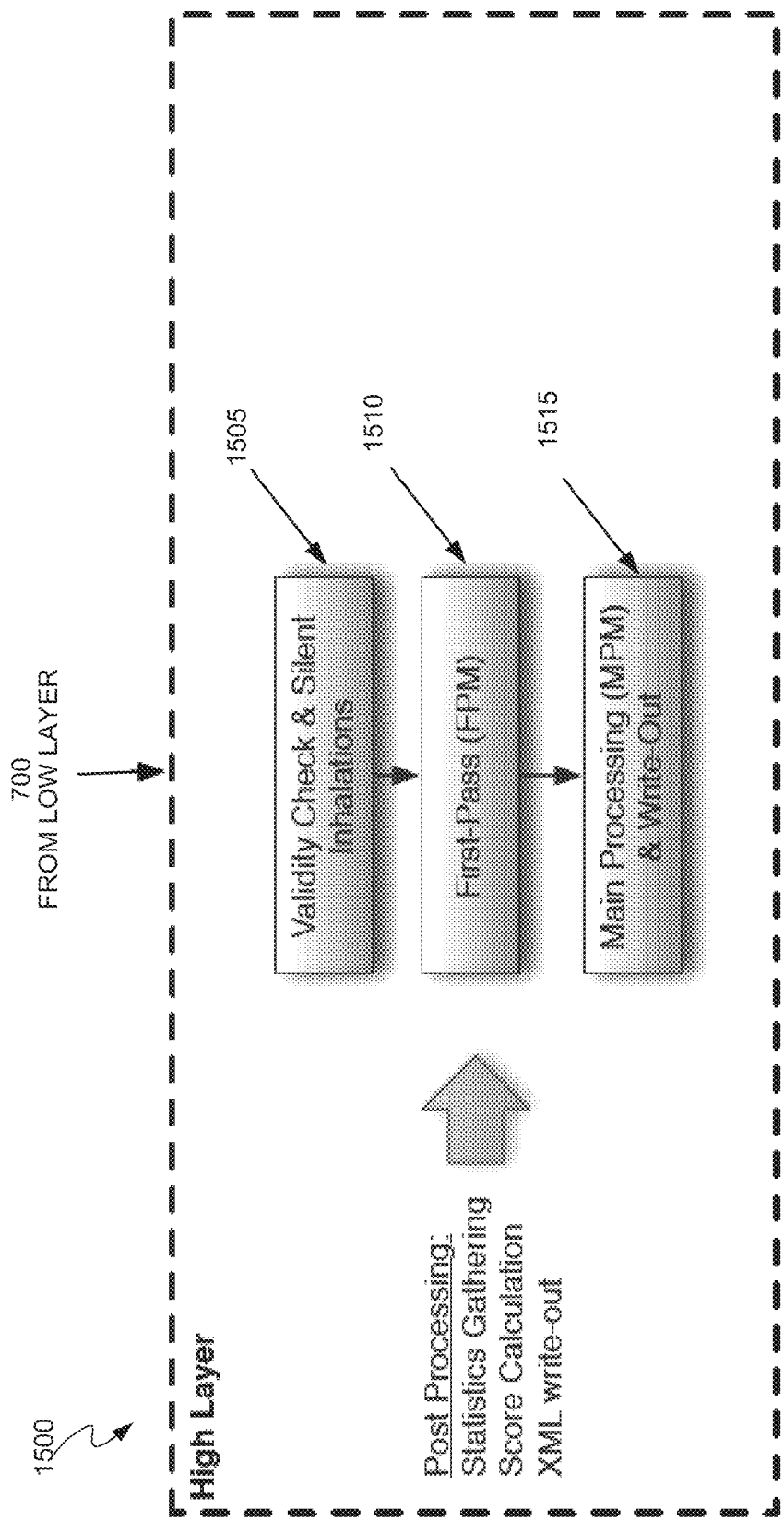
FIG. 15 illustrates a flowchart illustrating an exemplary structure of the high layer of the computer-implemented DRCT procedure in accordance with one embodiment of the present invention.

FIG. 15 illustrates a flowchart 1500 illustrating an exemplary structure of the high layer of the computer-implemented DRCT procedure in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 1500 should not be construed as limiting the scope of the invention. Rather, it will be apparent to persons skilled in the relevant art(s) from the teachings provided herein that other functional flows are within the scope and spirit of the present invention. Flowchart 1500 may be described with continued reference to exemplary embodiments described above, though the method is not limited to those embodiments.

At step 1505, a validity check is performed. The arrays from low layer 700 are checked for validity in terms of size and value range.

Further, depending on the silent inhalation flag and the compensation module activation, a pre-parsing of the detected breath cycle takes place. This includes checking for consecutive similar events, and focusing on the exhalation detection. The DRCT high layer procedure 1500, in one embodiment, tries to recreate a temporal plan of the distribution of the inhalations and to create an estimated full cycle vector (all breath events) to be used for the analysis. It should be noted that this procedure is only enabled when the information regarding the inhalations is so minimal or weak that full analysis would be impossible.

The first-pass module (FPM) at step 1510 comprises a stripped down version of the whole high-level module containing only the breath cycle event-based BPM (or RR) estimation. A FPM respiratory threshold is extracted and used in the second pass for threshold adjustments. This module enables the system to adjust and perform for sessions with a wide range of BPMs in a dynamic, session-specific manner.

The main process module (MPM) at step 1515 performs breath cycle separation which is done by event grouping. The MPM module processes a sequence vector with the event types, and outputs a breath cycle vector containing the map of all the events. Based on this separation, the MPM module performs a calculation of the full set of metrics by integrating auxiliary vectors related to the breath intensity, the wheeze, etc. into the breath cycle mapping. The following metrics are calculated per breath cycle and as a session average in the end for overall session analysis:

A) Average Respiratory Rate: The respiratory rate shows how fast or slow is the breathing in the session.

B) Respiratory Rate Variance: The variance refers to the deviation of each breath cycle from the session average. This is an indicator of the overall stability of the breathing patterns.

C) Deep/Shallow Metric: The depth of the breath is extracted mainly using the calculated duration and power intensity of each breath cycle.

D) Wheeze and Tension: Respiratory tension indicates the level of openness or constriction of the upper airways and throat. Nasal wheezing can indicate restriction or obstruction in the nasal passageways. Tracheal wheezing can indicate restriction or obstruction in the lungs. These are distinguished by a combination of intensity, duration and frequency content of the detected wheeze blocks.

E) Apnea refers to pauses of 10 seconds or more in between breaths following exhalation.

F) Pre-Apnea: Pre-Apnea refers to a pause of 2.5 seconds to 9.5 seconds and can be seen during waking hours, as well as be a precursor for clinical apnea.

G) Inhalation/Exhalation Ratio (IER): This is the ratio of the duration of the inhalation versus exhalation. These durations and their connection can help to extract conclusions about the breath patterns, specially concerning the physical state of the user. Other ratios can also be extracted such as the time of any one phase over the time of the total breath cycle. For example, the time of inhalation in relation to the time of the total breath cycle (Ti/Ttotal). These durations can indicate the physiological state of the user and can be correlated with physical and psychological indications and diagnosis.

H) Respiratory Flow: This metric indicates how choppy or smooth the breathing is. Choppy and smooth breathing patterns can have physical and physiological implications. For example, choppy breathing can indicate a disturbance in the respiratory movement musculature, the brain and nervous system, or the emotional state of the individual.

I) Number of Breaths: This metric is used to evaluate the validity of the session's results. Since analysis is displayed per breath cycle and as an average, the larger the number of cycles detected, the more statistically accurate the results will be.

The high layer 1500 will store all the statistics along with the breath phase durations for each breath cycle in an XML file that will be used to display the information to a user of the system.

II.D. Ventilatory Threshold Detection within the DRCT Framework

The conventional protocol for metabolic testing is to measure gas exchange values at rest for a specific duration and as the patient begins exercising with incremental power and intensity increases for specific time durations. The metabolic chart tracks how the gas exchange values change. In order to accomplish this with the respiratory acoustic analysis system of the present invention, first the breath phases, the breath cycle, and all the descriptors that characterize breathing at rest need to be determined using the DRCT framework described above. Then the change in the relevant descriptors can be tracked as the patient begins to exercise and increases exercise intensity.

The respiratory acoustic analysis system of the present invention is an alternative to the gas exchange methods which require a high level of precision, attention to detail and equipment that is quite expensive, all of which can be outside the range and skill set of the ordinary health fitness and clinical exercise physiology community. Alternatively, the present invention uses sounds created by the air moving into and out of the respiratory system. By analyzing breath sounds to detect breath cycle phases and frequency, volume, flow, and other characteristics, it is possible to characterize breathing at rest and during different exercise intensities to determine ventilatory thresholds.

The measurement of the ventilatory thresholds including but not limited to VT-aerobic (T1) and respiratory compensation (RCT-lactate or anaerobic, T2) thresholds and $VO_2$ Max using respiratory gas exchange is a standard diagnostic tool in exercise laboratories and is capable of defining important markers of sustainable exercise capacity, which may then be linked to the power output (PO) or heart rate (HR) response for training prescription. Measurement of respiratory gas exchange is cumbersome and expensive. Other important measurements that can be derived from respiratory gas exchange analysis include the amount of $O_2$ absorption in the blood and tissues, $VO_2$ max, the amount of fats and glucose utilized in metabolism.

Since the calculation of these metabolic thresholds is grounded in the volume, rate and pattern of breathing, as discussed in Section I. above, it is possible to use microphones to detect the breath sounds and acoustic analysis to derive estimates of ventilatory thresholds such as, but not limited to VT (T1) and RCT (T2), $O_2$ absorption, $VO_2$ MAX, the amount of fats and/or glucose utilized in metabolism at rest during incremental exercise and during all exercise intensities.

In one embodiment of the present invention, different subsets of the extracted metrics are used in the high layer 1500 to analyze and classify breathing patterns during different exercise intensities and during pulmonary testing. The high layer 1500 can be used, in one embodiment, to process the descriptor sequences from the low layer 700 by employing custom detection procedures in order to decide when the ventilatory thresholds occur. As discussed above, one embodiment of the present invention can be used to determine VT (T1) and RCT (T2). In a different embodiment, VT and RCT calculations can be made within the classifier core module 730 itself. Processes such as respiratory rate tracking and breath phase tracking and detection are important in the analysis as the final result is not only based on the overall breath sound statistics, but also on statistics that come from the analysis of each breath cycle as the breathing session progresses over time (e.g. inhalation intensity tracking).

Figure 16:
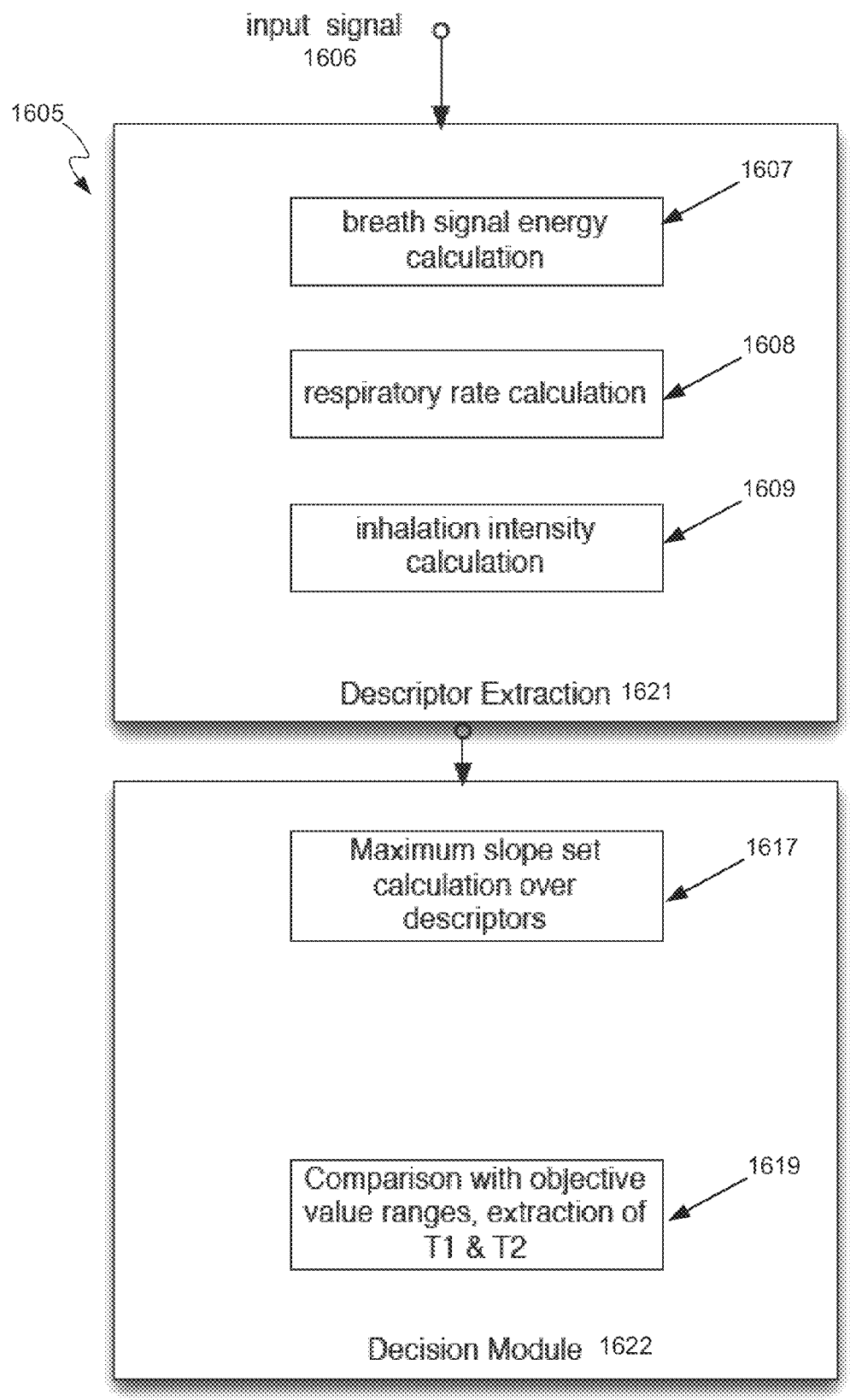
FIG. 16 depicts a framework for the ventilatory threshold calculation module in accordance with one embodiment of the present invention.

FIG. 16 depicts a framework 1605 for the ventilatory threshold calculation module in accordance with one embodiment of the present invention. The descriptor extraction module 1621, in one embodiment, extracts the descriptors needed from the input signal 1606 such as the breath signal energy 1607, the respiratory rate 1608 and the inhalation intensity 1609.

The VT and RCT usually coincide with the greatest changes in the respiratory rate. Accordingly, the decision module 1622 determines the maximum slope set 1617 over the descriptor set. Inhalation intensity is a useful descriptor because its values start going up when the subject expends the most effort in exercise. Hence, inhalation intensity is indicative of the RCT.

A comparison 1619 is then performed with objective value ranges before the final values of VT and RCT are extracted. The validation process comprises comparing the time stamps of the VT and RCT calculated by the framework 1605 with the VT (T1) and RCT (T2) as calculated using gas exchange measurements.

Figure 17:
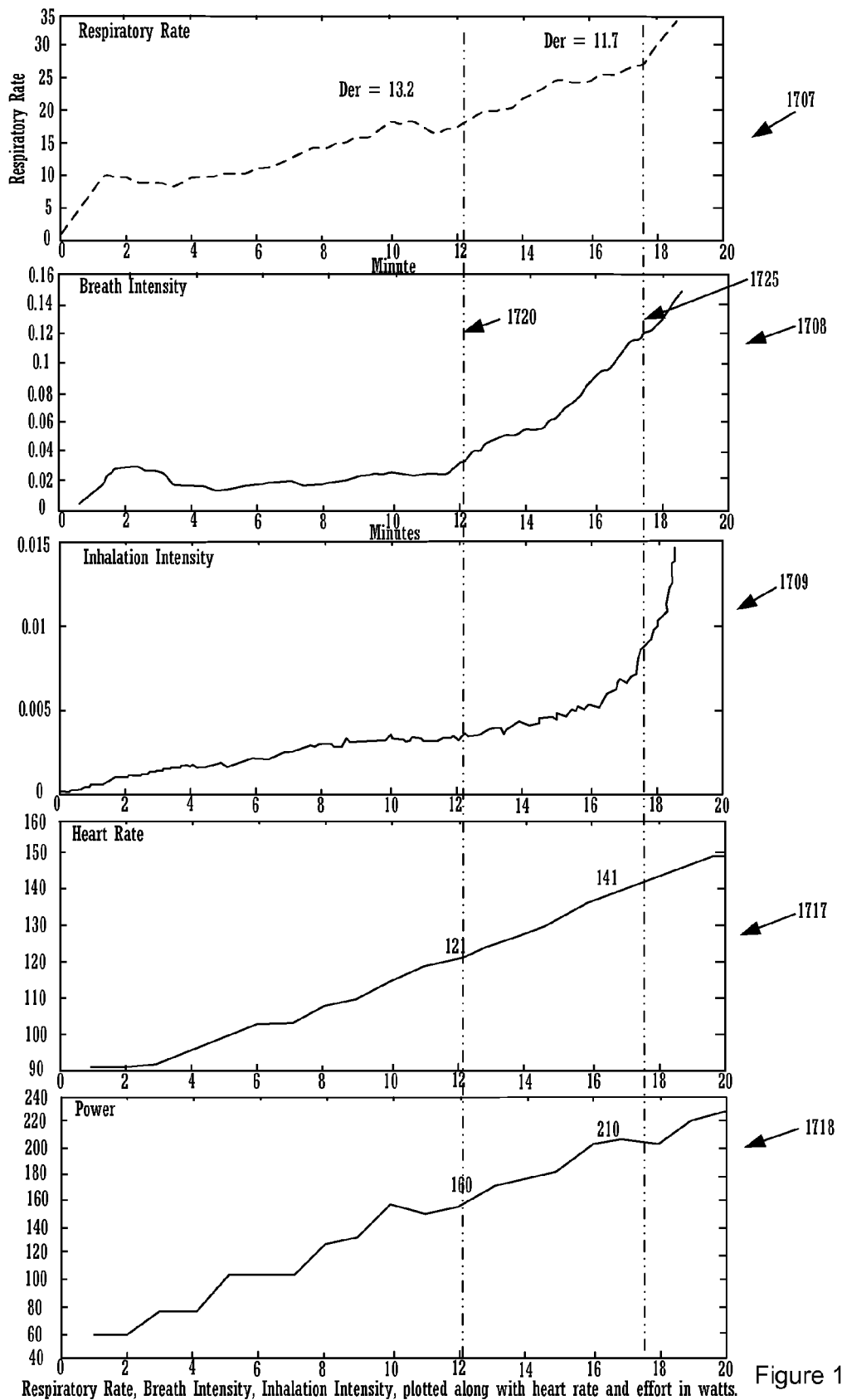
FIG. 17 depicts a graphical plot of respiratory rate, breath intensity, inhalation intensity, heart rate and effort versus time.

FIG. 17 depicts a graphical plot of respiratory rate, breath intensity, inhalation intensity, heart rate and effort versus time. The respiratory rate 1707, breath intensity 1708, inhalation intensity 1709, heart rate 1717 and power 1718 are all shown plotted against time. Time coordinates 1720 and 1725 correlate with VT and RCT because the derivative of the respiratory rate graph is highest at these coordinates and these coordinates also coincide with the greatest changes in the respiratory rate. Further, inhalation intensity as shown in graph 1709 starts to exponentially rise after coordinate 1725.

II.E. Miscellaneous Parameters

Figure 18:
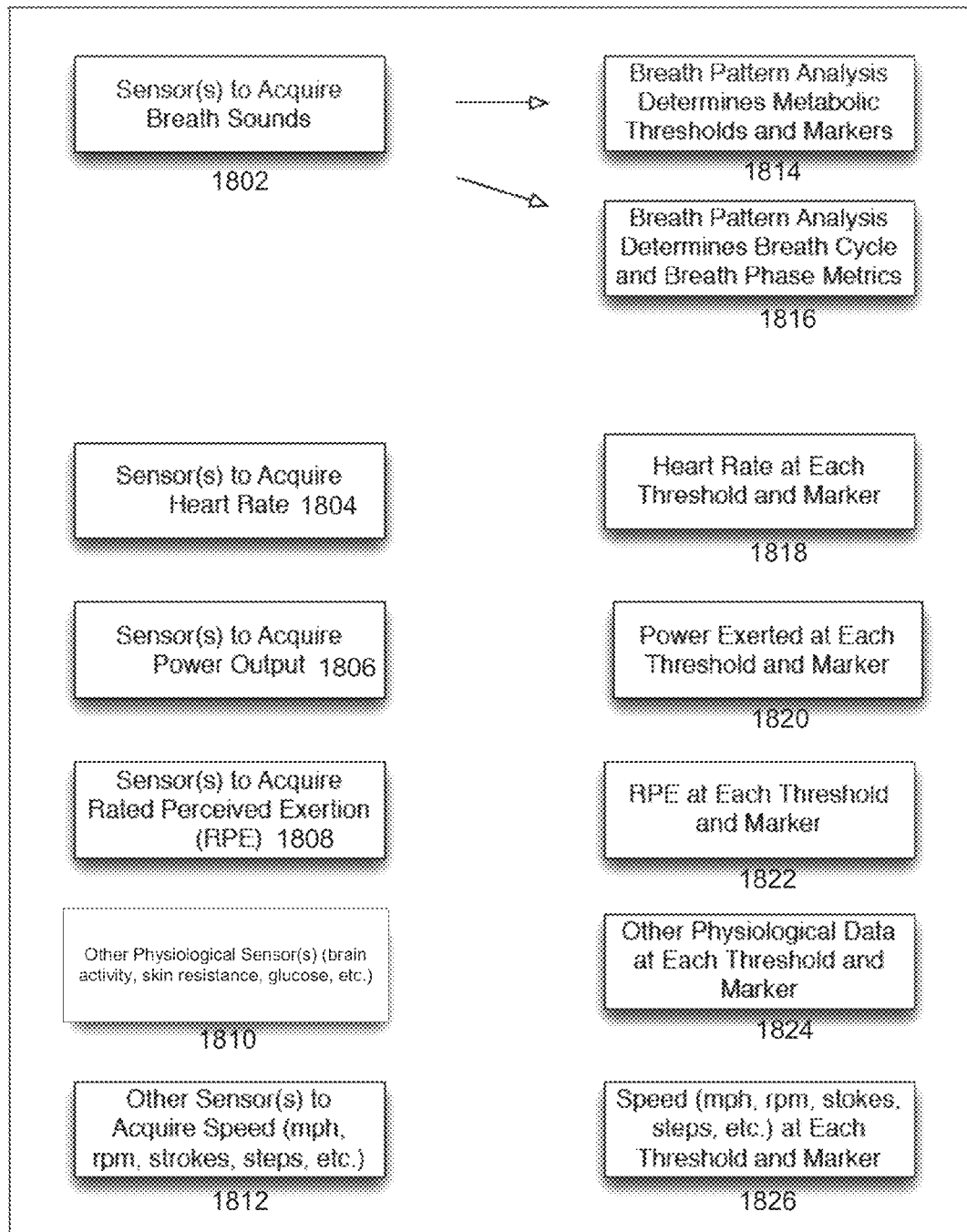
FIG. 18 illustrates additional sensors that can be connected to a subject to extract further parameters.

FIG. 18 illustrates additional sensors that can be connected to a subject to extract further parameters using the DRCT framework. Additional sensors 1810 for heart rate, power output, speed (mph, strokes, steps, etc.), brainwave activity, skin resistance, glucose, etc. are correlated to the ventilatory thresholds that are detected by the classifier core 730 to deliver a full report where several data points can be available.

Sensors to acquire breath sounds 1802 can be connected to a subject to perform breath pattern analysis and determine metabolic thresholds and markers 1814 and breath cycle and breath phase metrics 1816, as discussed above.

Further, sensors to acquire heart rate 1804 can be connected to determine heart rate at each threshold and marker 1818.

Sensors to acquire power output 1806 can be connected to the subject to extract information regarding power exerted at each threshold and marker 1820.

Sensors to acquire related perceived exertion (RPE) 1808 can be connected to derive RPE at each threshold and marker 1822.

Other physiological sensors e.g. brain activity, skin resistance, glucose, etc. can be connected to derive other physiological data at each threshold and marker 1824.

Finally, other sensors 1812 to acquire speed (mph, rpm, strokes, steps, etc.) can be used to derive speed (mph, rpm, strokes, steps, etc.) at each threshold and marker 1826.

In addition, input data regarding the user, client or patient including but not limited to gender, age, height, weight, fitness, level, nutrition, substance use (e.g. drugs, alcohol, smoking etc.), location, health info, lifestyle info, etc. can be used to determine a variety of metrics including ventilatory thresholds. The output data metrics can include, but are not limited to heart rate, power output, rated perceived exertion (RPE), speed of activity, cadence, breath cadence, calories, brain wave patterns, heart rate variability, heart training zones, respiratory training zones, resting metabolic rates, resting heart rate, resting respiratory rate, etc.

Cadence refers to the rhythm, speed, and/or rate of an activity and is frequently referred to in cycling and other sports. Breath cadence is the rhythm of breathing and can be compared to other rhythms including, but not limited to, rpm, strokes, steps, heart beat, etc.

Respiratory training zones can be calculated from the respiratory rates and other respiratory markets at the metabolic thresholds. Respiratory training zones of varying intensity could then be calculated.

The ventilatory response of a subject can be improved by optimizing the rate, depth, tension, flow, ramp, and breath phase relationships at different exercise intensities. Accordingly, the subject can produce more power, sustain exercise intensities longer (increase endurance), prolong or improve fat burning metabolism. Many techniques can be used to optimize ventilatory response including auditory, visual, kinesthetic real time and end time feedback, cueing, and coaching. Further, the ventilatory response can be optimized at different times, including, during different exercise intensities to get the most power, endurance, and speed, during recovery to get the best recovery (resting metabolic rate, resting heart rate, resting respiratory rate, and characteristics), and during any physical or mental activity to counter the negative effects of stress.

The delivery technology to allow a user to interact with the DRCT system and receive results can comprise wired sensors, wireless sensors, in-device analysis and display, cloud software in electronic portable device (e.g. mobile device, cell phone, tablet etc.), stand alone software, SaaS, embedded software into other tracking software, or embedded software on exercise, medical or health equipment.

II.F. User Interface

Figure 19:
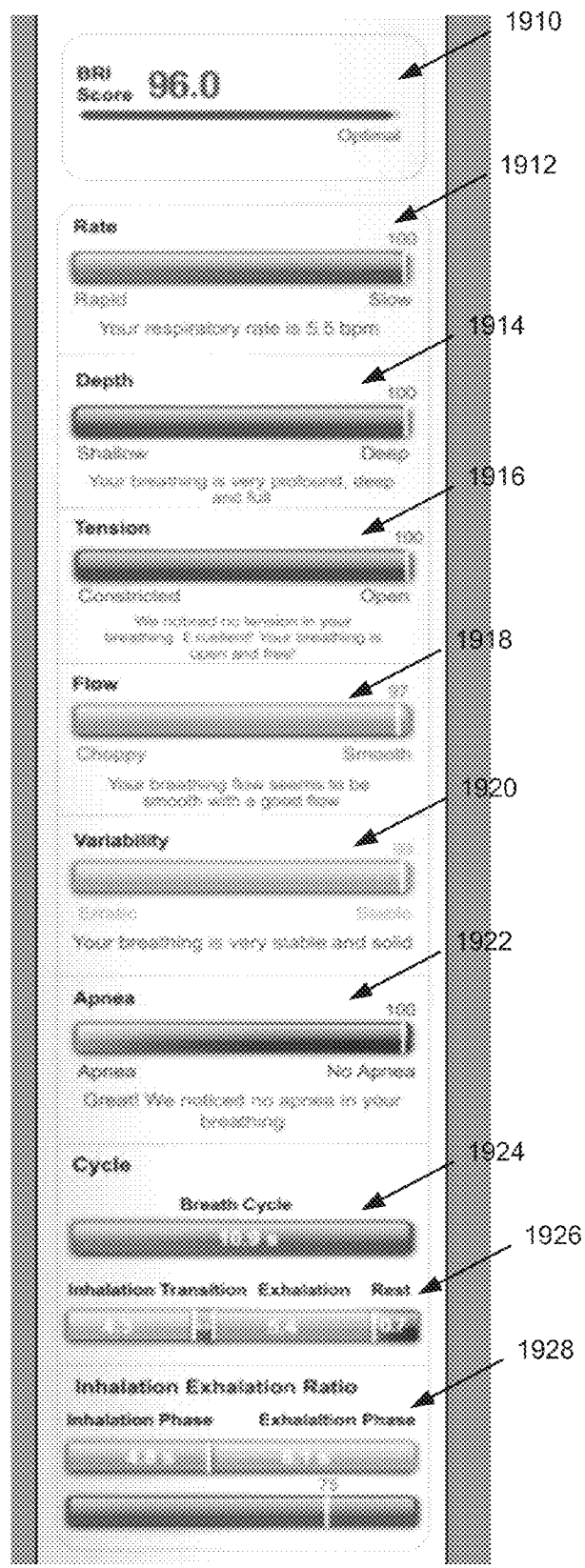
FIG. 19 shows a graphical user interface in an application supporting the DRCT framework for reporting the various metrics collected from the respiratory acoustic analysis in accordance with one embodiment of the present invention.

FIG. 19 shows a graphical user interface in an application supporting the high layer 1500 of the DRCT framework for reporting the various metrics collected from the respiratory acoustic analysis in accordance with one embodiment of the present invention.

The application for implementing the DRCT framework and performing the respiratory acoustic analysis of the present invention is operable to provide a user an interface for reporting the various statistics, metrics and parameters collected from the various analyses conducted using a subject's breath. This application can either be installed on a portable electronic device e.g. smart phone, tablet etc. connected to the microphone being used to capture the breathing sounds. Alternatively, it can be installed on a computing device such as a PC, notebook etc. that is either connected directly to the microphone or to a portable electronic device that is capturing the breathing sounds from the microphone.

The reporting interface of the application can assign a score 1910 to the subject's quality of breathing. It can also report other metrics and statistics, e.g., respiratory rate 1912, depth of breathing 1914, tension 1916, flow 1918, variability 1920, apnea 1922, breath cycle duration 1924, breath phase durations 1926, and inhalation/exhalation ratio (IER) 1928.

Figure 20:
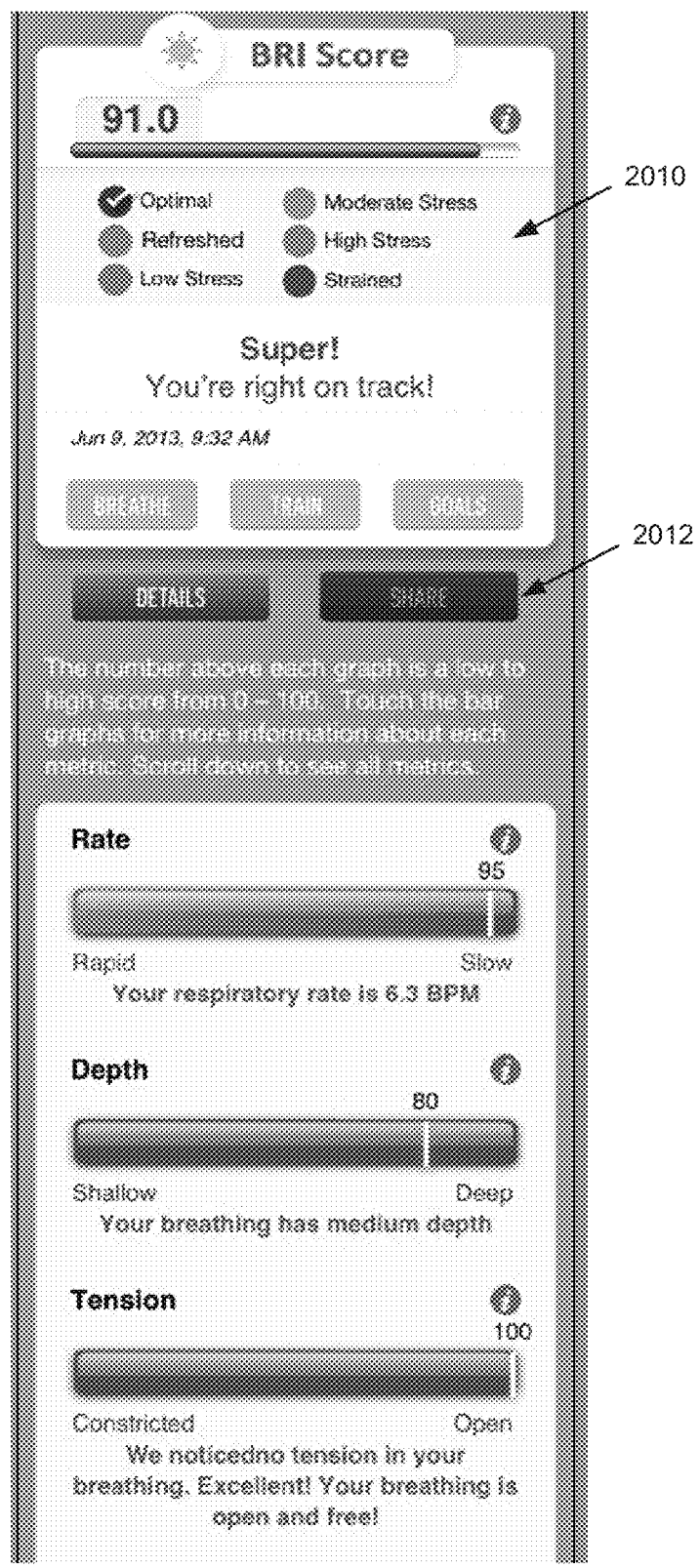
FIG. 20 illustrates a graphical user interface in an application supporting the DRCT framework for sharing the various metrics collected from the respiratory acoustic analysis in accordance with one embodiment of the present invention.

FIG. 20 illustrates a graphical user interface in an application supporting the DRCT framework for sharing the various metrics collected from the respiratory acoustic analysis in accordance with one embodiment of the present invention. In one embodiment, after the various metrics are reported, as illustrated in FIG. 19, they can be shared by the user by clicking an icon 2012 in the graphical user interface. The user, therefore, can share metrics related to the subject's breathing in addition to the score and performance level 2010 with other individuals through the user interface.

Figure 21:
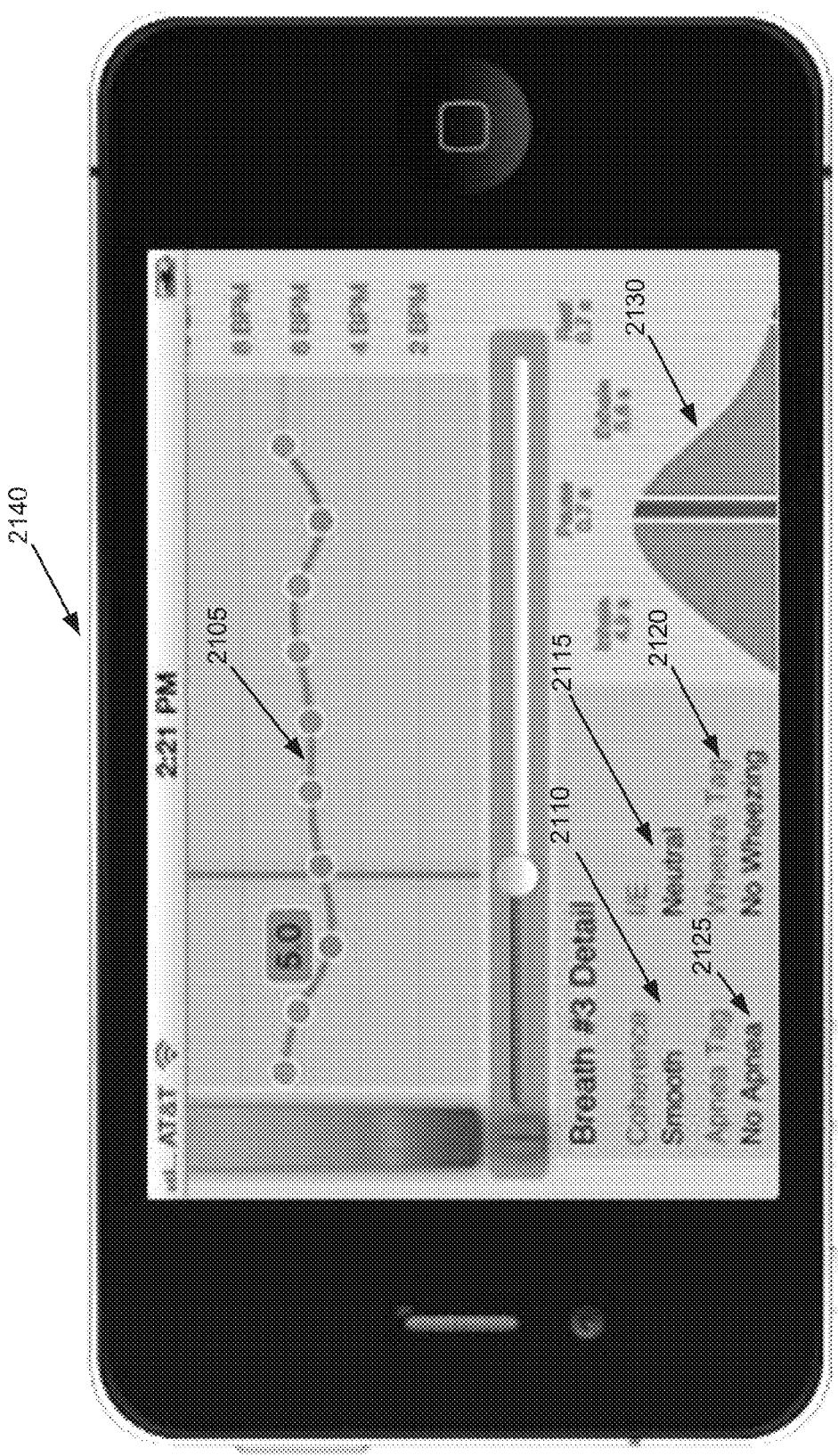
FIG. 21 illustrates an electronic apparatus running software to determine various breath related parameters in accordance with one embodiment of the present invention.

FIG. 21 illustrates an electronic apparatus running software to determine various breath related parameters in accordance with one embodiment of the present invention. The application for reporting the various metrics, as discussed above, can, in one embodiment, be installed on a portable electronic device such as a smart phone 2140. In addition to having the ability to report the various metrics and statistics discussed in connection with FIG. 19, the application can also illustrate the various metrics and statistics in graphical form, e.g., the breaths per minute (BPM) metric 2105 can be reported as a function of time as shown in FIG. 21. Further, information regarding other metrics such as coherence 2110, apnea 2125, wheezing 2120, IER 2115 can also be shown by the application. In one embodiment, a curve 2130 illustrating the durations of the various phases in a breath cycle can also be shown by the application.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered as examples because many other architectures can be implemented to achieve the same functionality.

The process parameters and sequence of steps described and/or illustrated herein are given by way of example only. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. These software modules may configure a computing system to perform one or more of the example embodiments disclosed herein. One or more of the software modules disclosed herein may be implemented in a cloud computing environment. Cloud computing environments may provide various services and applications via the Internet. These cloud-based services (e.g., software as a service, platform as a service, infrastructure as a service, etc.) may be accessible through a Web browser or other remote interface. Various functions described herein may be provided through a remote desktop environment or any other cloud-based computing environment.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as may be suited to the particular use contemplated.

Embodiments according to the invention are thus described. While the present disclosure has been described in particular embodiments, it should be appreciated that the invention should not be construed as limited by such embodiments, but rather construed according to the below claims.

What is claimed is:

1. A method for performing acoustic dynamic classification of a breathing session using a processor coupled to a memory, said method comprising:
  capturing breathing sounds of a subject using a microphone;
  processing said breathing sounds to generate an audio respiratory signal;

recognizing a plurality of breath cycles and a plurality of breath phases within each of said plurality of breath cycles from said audio respiratory signal;

detecting characteristics regarding said plurality of breath cycles and said plurality of breath phases; and extracting and outputting metrics concerning a breath pattern quality of said subject using said characteristics wherein said metrics are selected from a group consisting of: respiratory rate; depth; tension; nasal wheeze; tracheal wheeze; pre-apnea; apnea; ramp; flow; variability; and inhale/exhale ratio;

wherein said recognizing comprises:
obtaining a first audio envelope by filtering an audio respiratory signal, wherein said obtaining comprises calculating a spectral centroid of each block of said audio respiratory signal and filtering said audio respiratory signal with a low pass filter tuned to a minimum value of said spectral centroid;

classifying lobes of said first audio envelope into a plurality of classes; and defining said plurality of breath cycles and said plurality of breath phases using timestamps obtained from said classifying.

2. The method of claim 1, wherein each breath phase within said plurality of breath phases is selected from a group consisting of: inhale; transition; exhale and rest.

3. The method of claim 1, wherein each class within said plurality of classes is selected from a group consisting of: inhalations; exhalations; rest periods.

4. The method of claim 1, wherein said classifying comprises:
calculating a second audio envelope using a window, wherein said window has a size set according to a respiratory rate;
normalizing said second audio envelope;
detecting peaks of said second audio envelope;
determining a start timestamp and an end timestamp of each breath cycle using said peaks; and
calculating a low threshold and a high threshold by using a moving average filter on said second audio envelope, wherein said low threshold detects signal presence, and further wherein said high threshold discriminates between inhalation and exhalation events.

5. The method of claim 4, wherein calculating said respiratory rate comprises:
calculating an auto-correlation function (ACF) of said first audio envelope; and
determining a peak of said ACF; and
using said peak to determine said respiratory rate.

6. The method of claim 5, wherein said respiratory rate is used to determine a ventilatory threshold wherein said ventilatory threshold occurs when a rate of change of said respiratory rate is greatest.

7. The method of claim 1, wherein said characteristics are selected from a group consisting of: inhale duration, pause duration, exhale duration, rest duration, a wheeze source, a wheeze type, a cough type, a cough source, choppiness, smoothness, attack and decay.

8. The method of claim 1, wherein at least one of said characteristics is wheezing, and wherein said detecting comprises:
analyzing a block of said audio respiratory signal;
calculating an auto-correlation function (ACF) for said block;
calculate a linear predictive coefficient (LPC) for said block;

generating an inverse LPC filter along with a magnitude response for each block; and
analyzing said ACF and said magnitude response to identify said wheezing.

9. The method of claim 1, wherein at least one characteristic is coughing, and wherein said detecting comprises:
extracting a first plurality of descriptors that define a cough pattern from said audio respiratory signal;
comparing said first plurality of descriptors to a database comprising a second plurality of descriptors extracted from sample coughs; and
mapping an input cough from said audio respiratory signal to a closest match from said database.

10. The method of claim 9, wherein said descriptors are selected from a group consisting of: attack time; decay time; envelope intensity; spectral centroid; spectral spread; spectral kyrtosis; and harmonicity.

11. The method of claim 10, wherein said descriptors are used to perform a spirometry analysis.

12. The method of claim 1, wherein said descriptors can be used to determine a respiratory compensation threshold (RCT).

13. A computer-readable storage medium having stored thereon, computer executable instructions that, if executed by a computer system cause the computer system to perform a method for performing acoustic dynamic classification of a breathing session using a processor coupled to a memory, said method comprising:
capturing breathing sounds of a subject using a microphone;
processing said breathing sounds to generate an audio respiratory signal;
recognizing a plurality of breath cycles and a plurality of breath phases within each of said plurality of breath cycles from said audio respiratory signal;
detecting characteristics regarding said plurality of breath cycles and said plurality of breath phases; and
extracting and outputting metrics concerning a breath pattern quality of said subject using said characteristics wherein said metrics are selected from a group consisting of: respiratory rate; depth; tension; nasal wheeze; tracheal wheeze; pre-apnea; apnea; ramp; flow; variability; and inhale/exhale ratio;
wherein said recognizing comprises:
obtaining a first audio envelope by filtering an audio respiratory signal, wherein said obtaining comprises calculating a spectral centroid of each block of said audio respiratory signal and filtering said audio respiratory signal with a low pass filter tuned to a minimum value of said spectral centroid;
classifying lobes of said first audio envelope into a plurality of classes; and
defining said plurality of breath cycles and said plurality of breath phases using timestamps obtained from said classifying.

14. The computer-readable medium as described in claim 13, wherein said classifying comprises:
calculating a second audio envelope using a window, wherein said window has a size set according to a respiratory rate;
normalizing said second audio envelope;
detecting peaks of said second audio envelope;
determining a start timestamp and an end timestamp of each breath cycle using said peaks; and
calculating a low threshold and a high threshold by using a moving average filter on said second audio envelope, wherein said low threshold detects signal presence, and further wherein said high threshold discriminates between inhalation and exhalation events.

15. The computer-readable medium as described in claim 14, wherein calculating said respiratory rate comprises:
calculating an auto-correlation function (ACF) of said first audio envelope; and
determining a peak of said ACF; and
using said peak to determine said respiratory rate.

16. The computer-readable medium as described in claim 13, wherein at least one of said characteristics is wheezing, and wherein said detecting comprises:
analyzing a block of said audio respiratory signal;
calculating an auto-correlation function (ACF) for said block;
calculating a linear predictive coefficient (LPC) for said block;
generating an inverse LPC filter along with a magnitude response for each block; and
analyzing said ACF and said magnitude response to identify said wheezing.

17. An apparatus for performing acoustic dynamic classification of a breathing session, said apparatus comprising:
a microphone for capturing breathing sounds of a subject;
a memory comprises an application for performing dynamic classification of a breathing session stored therein; and
a processor coupled to said memory and said microphone, the processor being configured to operate in accordance with said application to:
process said breathing sounds to generate an audio respiratory signal;
recognize a plurality of breath cycles and a plurality of breath phases within each of said plurality of breath cycles from said audio respiratory signal;
detect characteristics regarding said plurality of breath cycles and said plurality of breath phases; and
extract and output metrics concerning a breath pattern quality of said subject using said characteristics wherein said metrics are selected from a group consisting of: respiratory rate; depth; tension; nasal wheeze; tracheal wheeze; pre-apnea; apnea; ramp; flow; variability; and inhale/exhale ratio;
wherein to recognize said plurality of breath cycles and said plurality of breath phases, said processor is configured to:
obtain a first audio envelope from said audio respiratory signal by calculating a spectral centroid of each block of said audio respiratory signal and filtering said audio respiratory signal with a low pass filter tuned to a minimum value of said spectral centroid;
classify lobes of said first audio envelope into a plurality of classes; and
define said plurality of breath cycles and said plurality of breath phases using timestamps obtained from said classifying.

* * * * *